(12) United States Patent
Swami et al.

(10) Patent No.: US 12,031,896 B2
(45) Date of Patent: Jul. 9, 2024

(54) METHOD AND SYSTEM FOR IMPEDANCE-BASED QUANTIFICATION AND MICROFLUIDIC CONTROL

(71) Applicant: UNIVERSITY OF VIRGINIA PATENT FOUNDATION, Charlottesville, VA (US)

(72) Inventors: Nathan Swami, Charlottesville, VA (US); Walter Varhue, Charlottesville, VA (US); Vahid Farmehini, Charlottesville, VA (US)

(73) Assignee: UNIVERSITY OF VIRGINIA PATENT FOUNDATION, Charlottesville, VA (US)

( * ) Notice: Subject to any disclaimer, the term of this patent is extended or adjusted under 35 U.S.C. 154(b) by 338 days.

(21) Appl. No.: 17/425,414

(22) PCT Filed: Jan. 24, 2020

(86) PCT No.: PCT/US2020/014899
§ 371 (c)(1),
(2) Date: Jul. 23, 2021

(87) PCT Pub. No.: WO2020/154566
PCT Pub. Date: Jul. 30, 2020

(65) Prior Publication Data
US 2022/0091014 A1  Mar. 24, 2022

Related U.S. Application Data

(60) Provisional application No. 62/796,317, filed on Jan. 24, 2019.

(51) Int. Cl.
B01L 3/00 (2006.01)
G01N 15/01 (2024.01)
(Continued)

(52) U.S. Cl.
CPC .... *G01N 15/1031* (2013.01); *B01L 3/502715* (2013.01); *B01L 3/502761* (2013.01);
(Continued)

(58) Field of Classification Search
CPC ........... G01N 15/1031; G01N 33/4833; G01N 2015/0065; B01L 3/502715;
(Continued)

(56) References Cited

U.S. PATENT DOCUMENTS 5,631,165 A   5/1997  Chupp et al.
8,309,930 B2  11/2012 Gelmont et al.
(Continued)

FOREIGN PATENT DOCUMENTS

EP       2259044      12/2010
WO    2008/109706    9/2008
(Continued)

OTHER PUBLICATIONS

International Search Report and Written Opinion, issued in PCT/US2020/014899, dated Apr. 24, 2020, 10 pages.
(Continued)

*Primary Examiner* — Alexander Satanovsky
*Assistant Examiner* — Trung Q Nguyen
(74) *Attorney, Agent, or Firm* — Meunier Carlin & Curfman LLC

(57) ABSTRACT

Disclosed herein are methods and systems that facilitate the integration of on-chip impedance sensors and measurement circuitries for quantifying the impedance/frequency response of microfluidic device under the same, or similar, conditions used for particle manipulation. The methods and systems can use a microfluidic chip comprising a microfluidic channel with one or more electric-field-generating structures located therein, including a first electric-field-generating structure, wherein the one or more electric-field-
(Continued)

generating structures is configured to selectively polarize or manipulate biologic or particle components flowing within the microfluidic channel. The method and system can also employ a circuit configured for automated determination and quantification of parasitic voltage drops during AC electrokinetic particle manipulation, without the need to use valuable biological samples or model particles. The determined impedance response can be used to assess efficacy of the microfluidic device geometry as well as to provide control signals to inform downstream cell separation decisions.

21 Claims, 21 Drawing Sheets

(51) Int. Cl.
    G01N 15/1031    (2024.01)
    G01N 33/483    (2006.01)
    G01R 27/16    (2006.01)
(52) U.S. Cl.
    CPC ......... G01N 33/4833 (2013.01); G01R 27/16 (2013.01); *B01L 2200/0647* (2013.01); *B01L 2300/0627* (2013.01); *G01N 15/01* (2024.01)
(58) Field of Classification Search
    CPC ....... B01L 3/502761; B01L 2200/0647; B01L 2300/0627; G01R 27/16; B03C 5/005; B03C 5/026; B03C 2201/26
    USPC ....... 324/600, 617–622, 650, 500, 521, 683, 324/76.11, 76.52, 76.53, 76.77, 757.05, 324/762.06
    See application file for complete search history.

(56) References Cited

U.S. PATENT DOCUMENTS

| | | | |
|---|---|---|---|
| 8,525,115 | B1 | 9/2013 | Gelmont et al. |
| 10,024,780 | B2 | 7/2018 | Shah et al. |
| 11,339,417 | B2 | 5/2022 | Swami et al. |
| 2012/0085649 | A1* | 4/2012 | Sano ........................ B03C 5/005 204/547 |
| 2012/0142032 | A1 | 6/2012 | Morgan et al. |
| 2015/0158028 | A1 | 6/2015 | Hadwen |
| 2017/0218424 | A1 | 8/2017 | Swami et al. |
| 2019/0137443 | A1* | 5/2019 | Balijepalli ............. G01N 27/62 |
| 2020/0353469 | A1 | 11/2020 | Swami et al. |

FOREIGN PATENT DOCUMENTS

| | | |
|---|---|---|
| WO | 2016/057974 | 4/2016 |
| WO | 2017/184854 | 10/2017 |
| WO | 2018/200872 | 11/2018 |
| WO | 2020/069185 | 4/2020 |

OTHER PUBLICATIONS

Extended European Search Report issued for Application No. 20745971, dated Sep. 16, 2022.
Adams, T. N.; Jiang, A. Y.; Vyas, P. D.; Flanagan, L. A., "Separation of neural stem cells by whole cell membrane capacitance using dielectrophoresis," Methods, 133, 91-103 (2018).
Barbulovic-Nad, I.; Xuan, X.; Lee, J. S.; Li, D., "DC dielectrophoretic separation of microparticles using an oil droplet obstacle," Lab on a Chip, 6 (2), 274-279 (2006).
Baret, J.-C.; Miller, O. J.; Taly, V.; Ryckelynck, M.; El-Harrak, A.; Frenz, L.; Rick, C.; Samuels, M. L.; Hutchison, J. B.; Agresti, J. J., "Fluorescence-activated droplet sorting (FADS): efficient microfluidic cell sorting based on enzymatic activity," Lab on a Chip, 9 (13), 1850-1858 (2009).
Bodas, D.; Khan-Malek, C., "Hydrophilization and hydrophobic recovery of PDMS by oxygen plasma and chemical treatment—An SEM investigation," Sensors and Actuators B: Chemical, 123 (1), 368-373 (2007).
Bruus, H.; Dual, J.; Hawkes, J.; Hill, M.; Laurell, T.; Nilsson, J.; Radel, S.; Sadhal, S.; Wiklund, M., "Forthcoming Lab on a Chip tutorial series on acoustofluidics: Acoustofluidics—exploiting ultrasonic standing wave forces and acoustic streaming in microfluidic systems for cell and particle manipulation," Lab on a Chip, 11 (21), 3579-3580 (2011).
Burgarella, S.; Merlo, S.; Figliuzzi, M.; Remuzzi, A., "Isolation of L angerhans islets by dielectrophoresis," Electrophoresis, 34 (7), 1068-1075 (2013).
Choi, K.; Ng, A. H.; Fobel, R.; Wheeler, A. R., "Digital microfluidics," Annual review of analytical chemistry, 5, 413-440 (2012).
Dual, J.; Hahn, P.; Leibacher, I.; Möller, D.; Schwarz, T., "Acoustofluidics 6: Experimental characterization of ultrasonic particle manipulation devices," Lab on a Chip, 12 (5), 852-862 (2012).
Farmehini, V.; Rohani, A.; Su, Y.- H.; Swami, N. S., "A wide-bandwidth power amplifier for frequency-selective insulator-based dielectrophoresis," Lab on a Chip, 14 (21), 4183-4187 (2014).
Fernandez, R. E.; Rohani, A.; Farmehini, V.; Swami, N. S., "Microbial analysis in dielectrophoretic microfluidic systems," Analytica chimica acta, 966, 11-33 (2017).
Green, N. G.; Ramos, A.; Morgan, H., "Ac electrokinetics: a survey of submicrometre particle dynamics," Journal of Physics D: Applied Physics, 33 (6), 632 (2000).
Hammarström, B.; Evander, M.; Wahlström, J.; Nilsson, J., "Frequency tracking in acoustic trapping for improved performance stability and system surveillance," Lab on a Chip, 14 (5), 1005-1013 (2014).
Hanson, C.; Vargis, E., "Alternative cdep design to facilitate cell isolation for identification by Raman spectroscopy," Sensors, 17 (2), 327 (2017).
Horowitz, P.; Hill, W.; Robinson, I., The art of electronics. Cambridge university press Cambridge vol. 2 (1980).
Huang, Y.; Wang, X.- B.; Gascoyne, P. R.; Becker, F. F., "Membrane dielectric responses of human T-lymphocytes following mitogenic stimulation," Biochimica et Biophysica Acta (BBA)-Biomembranes, 1417 (1), 51-62 (1999).
Hunt, T. P.; Issadore, D.; Westervelt, R. M., "Integrated circuit/microfluidic chip to programmably trap and move cells and droplets with dielectrophoresis," Lab on a Chip, 8 (1), 81-87 (2008).
Li, M.; Anand, R. K., "High-throughput selective capture of single circulating tumor cells by dielectrophoresis at a wireless electrode array," Journal of the American Chemical Society, 139 (26), 8950-8959 (2017).
Link, D. R.; Grasland-Mongrain, E.; Duri, A.; Sarrazin, F.; Cheng, Z.; Cristobal, G.; Marquez, M.; Weitz, D. A., "Electric control of droplets in microfluidic devices,". Angewandte Chemie International Edition, 45 (16), 2556-2560 (2006).
Madiyar, F. R.; Bhana, S.; Swisher, L. Z.; Culbertson, C. T.; Huang, X.; Li, J., "Integration of a nanostructured dielectrophoretic device and a surface-enhanced Raman probe for highly sensitive rapid bacteria detection," Nanoscale, 7 (8), 3726-3736 (2015).
McLucas, J., "Precision peak detector uses no precision components," Cahnersdenver Publishing Co (2004).
Moraes, C.; Sun, Y.; Simmons, C. A., "Solving the shrinkage-induced PDMS alignment registration issue in multilayer soft lithography," Journal of micromechanics and microengineering, 19 (6), 065015 (2009).
Rohani, A.; Moore, J. H.; Kashatus, J. A.; Sesaki, H.; Kashatus, D. F.; Swami, N. S., "Label-free quantification of intracellular mitochondrial dynamics using dielectrophoresis," Analytical chemistry 89 (11), 5757-5764 (2017).
Rohani, A.; Sanghavi, B. J.; Salahi, A.; Liao, K.-T.; Chou, C.-F.; Swami, N. S., "Frequency-selective electrokinetic enrichment of biomolecules in physiological media based on electrical double-layer polarization," Nanoscale, 9 (33), 12124- 12131 (2017).
Salmanzadeh, A.; Romero, L.; Shafiee, H.; Gallo-Villanueva, R. C.; Stremler, M. A.; Cramer, S. D.; Davalos, R. V., "Isolation of prostate tumor initiating cells (TICs) through their dielectrophoretic signature," Lab on a Chip, 12 (1), 182-189 (2012).

(56) References Cited

OTHER PUBLICATIONS

Sano, M. B.; Salmanzadeh, A.; Davalos, R. V., "Multilayer contactless dielectrophoresis: Theoretical considerations," Electrophoresis, 33 (13), 1938-1946 (2012).
Shafiee, H.; Caldwell, J. L.; Sano, M. B.; Davalos, R. V., "Contactless dielectrophoresis: a new technique for cell manipulation," Biomedical microdevices, 11 (5), 997 (2009).
Varhue, W. B.; Langman, L.; Kelly-Goss, M.; Lataillade, M.; Brayman, K. L.; Peirce-Cottler, S.; Swami, N. S., "Deformability-based microfluidic separation of pancreatic islets from exocrine acinar tissue for transplant applications," Lab on a Chip, 17 (21), 3682-3691 (2017).
Walling, M. A.; Shepard, J. R., "Cellular heterogeneity and live cell arrays," Chemical Society Reviews, 40 (7), 4049-4076 (2011).
Zellner, P.; Shake, T.; Sahari, A.; Behkam, B.; Agah, M., "Offchip passivatedelectrode, insulator-based dielectrophoresis (OπDEP)," Analytical and bioanalytical chemistry, 405 (21), 6657-6666 (2013).
Zhu, X .; Tung, K.- W.; Chiou, P.-Y., "Heavily doped silicon electrode for dielectrophoresis in high conductivity media," Applied Physics Letters, 111 (14), 143506 (2017).
Kashatus, Jennifer A., et al. "Erk2 phosphorylation of Drp1 promotes mitochondrial fission and MAPK-driven tumor growth." Molecular cell 57.3 (2015): 537-551.
Sun, Tao, and Hywel Morgan. "Single-cell microfluidic impedance cytometry: a review." Microfluidics and Nanofluidics 8 (2010): 423-443.
Communication pursuant to Article 94(3) EPC issued in EP 20745971.0, dated Dec. 7, 2023.

\* cited by examiner

METHOD AND SYSTEM FOR IMPEDANCE-BASED QUANTIFICATION AND MICROFLUIDIC CONTROL

CROSS-REFERENCE TO RELATED APPLICATION

This is a national phase application filed under 35 U.S.C. § 371 of PCT International Application No. PCT/US2020/014899, filed Jan. 24, 2020, entitled "METHOD AND SYSTEM FOR IMPEDANCE-BASED QUANTIFICATION AND MICROFLUIDIC CONTROL," which claims priority to and benefit under 35 U.S.C § 119(e) of U.S. Provisional Patent Application Ser. No. 62/796,317, entitled "System and Method for Quantifying the Response of Electrical Field Penetration for Optimizing Particle Manipulation in Microfluidic Devices," filed Jan. 24, 2019, each of which is hereby incorporated by reference herein in its entirety.

STATEMENT OF GOVERNMENT INTEREST

This invention was made with government support under Grant No. AI130902 awarded by The National Institutes of Health. The government has certain rights in the invention.

FIELD

This disclosure relates to impedance characterization of internal microfluidic structures and the cytometric characterization of cells or particles, based on their impedance response.

BACKGROUND

Electrical fields are widely used within microfluidic devices to selectively polarize and manipulate micro- and nanoscale objects using dielectrophoresis (DEP), such as biomolecules, viruses, bacteria, mammalian cells, multi-cell aggregates, and aqueous droplet suspensions in oil. Because electrical fields are facile to integrate within microfluidic channels to locally cause particle deflection from flow streamlines and can enable frequency selective polarization of the micro- or nanoscale objects in a label-free manner based on the conductivity and permittivity of their contents, microfluidic devices configured with electric-field-generating structures are preferably in used in many applications. Electric field generated by electrodes defined in such structures is applied through an insulating barrier, which isolates the electrode region from the sample manipulation region. Example of such configurations may be found in microfluidic chips configured for contactless dielectrophoresis (cDEP), bipolar electrode DEP, passivated electrode DEP, electrowetting on dielectric, and droplet manipulation systems.

Selective manipulation of cells, bacteria and nano-colloids within microsystems under electrical, inertial and acoustic force fields for particle separation and isolation requires microstructures that are generally fabricated to high fidelity. Conventional method to assess functionality of manufactured microfluidic devices often involves the imaging of the trapping of model particles within each device under the requisite force fields. In addition to requiring extensive microscopy to be conducted in a manufacturing space, the technique employs valuable biological samples and the reliance on a trained operator to assess the efficacy of trapping, which often fails to identify the particular microfabrication failure.

SUMMARY

An exemplary method and system is disclosed that facilitate the integration of on-chip impedance sensors and measurement circuitries, e.g., in characterizing internal microfluidic structures and/or in cell or particle cytometry, for quantifying the impedance/frequency response of microfluidic device under the same, or similar, conditions used for particle manipulation. In some embodiments, the exemplary method and system employs a circuit configured for automated determination and quantification of parasitic voltage drops during AC electrokinetic particle manipulation, without the need to use valuable biological samples or model particles. The determined impedance response can be used to assess efficacy of the microfluidic device geometry as well as to provide control signals to inform downstream cell separation decisions.

The term "on-chip", as used herein, refers to a microfluidic circuit structure (e.g., microfluidic chip) that is mechanically and electronically integrated with electronic circuit components to form a fully integrated unit that includes all components necessary to measure and/or assess impedance spectra for the geometric or functional quantification of internal structures of the microfluidic chip and/or to measure and/or assess the impedance characteristics of the biologic or particle components to control polarization or manipulation of the biologic or particle components.

In some embodiments, the exemplary method and system employs a circuit that directly interfaces to the microfluidic device to measure impedance at the AC power levels and wide frequency ranges used for DEP manipulation (20-200 Vpp/cm over 0.1-10 MHz).

To assess the efficacy of the microfluidic device geometry, the exemplary method and system employs automated fitting operation of the measured impedance spectra to an equivalent circuit model of the microfluidic device geometry comprising, in some embodiments, the resistance and capacitance values of each layer of the microfabricated device geometry, such as width, surface area and surface charge distribution of the insulating barrier and architecture of the sample and electrode channels, to assess variations in such geometry. Based on such quantification and assessment, the device geometry and stimulation conditions can be adjusted and/or designed to maximize fraction of the applied voltage available for DEP manipulation and to temporally alter the separation characteristics. In some embodiments, the voltage fraction for DEP manipulation may be determined from the impedance frequency response after accounting for the parasitic voltage drops and is correlated to the determined levels of DEP trapping, so that the device geometry can be optimized to maximize trapping. In some embodiments, the equivalent circuit model is used to assess the geometry and the parasitic voltages in devices with varying levels of misalignment and sample channel architecture.

To provide control signals for the control of the polarization or manipulation of the biologic or particle components, the exemplary method and system, in some embodiments, employs an on-chip measurement and assessment of impedance spectra of sample characteristics to which automated fitting operation of the measured impedance spectra to an equivalent circuit model of sample characteristics is applied to rapidly inform downstream decisions on particle or cell manipulation.

An exemplary method and system may be used for electrokinetic manipulation over an insulated channel in a contact-less dielectrophoresis mode to assess, via impedance-based assessment, interlayer mis-alignments and variations in channel dimensions for quantifying the parasitic voltage drops and maximizing fraction of the applied voltage available for dielectrophoretic manipulation. Indeed, such electrical characterization approaches may be routinely conducted for quality assurance of manufactured microfluidic devices.

In an aspect, a method is disclosed comprising providing a microfluidic chip, the microfluidic chip comprising a microfluidic channel with one or more electric-field-generating structures located therein, including a first electric-field-generating structure (e.g., electrodes), wherein the one or more electric-field-generating structures is configured to selectively polarize or manipulate biologic or particle components flowing within the microfluidic channel; and measuring, via an on-chip impedance sensing element (e.g., on-chip resister), impedance spectra associated with at least one internal capacitive structure (e.g., parasitic voltage due to at least one capacitive structure) of the first electric-field-generating structure or characteristic of the biologic or particle components, wherein the measured impedance spectra is used at least for one of i) control of the polarization or manipulation of the biologic or particle components when flowing through the microfluidic channel and ii) geometric or functional quantification of the at least one internal capacitive structure or of the microfluidic chip.

In some embodiments, the method further includes triggering, by a processor or control circuit, controls of the polarization or manipulation of the biologic or particle components when flowing through the microfluidic channel based on the measured impedance spectra (e.g., which provides a quantification of media conductivity of biologic or particle components or provide an identification of the type of biologic or particle components).

In some embodiments, the method further includes determining, via a processor or logic circuit, one or more parameters associated with the at least one internal capacitive structure, wherein the one or more parameters is selected from the group consisting of: an associated thickness of the at least one capacitive structure (e.g., thickness at a thinnest or thickest portion of the insulating barrier); a surface area size of the at least one internal capacitive structure; a surface charge property of the at least one internal capacitive structure; an architecture feature of the at least one internal capacitive structure; and a size of a portion of microfluidic channel to which the first electric-field-generating structure is located.

In some embodiments, the method further includes determining, via a processor or logic circuit, one or more parameters associated with the at least one internal capacitive structure or the characteristic of the biologic or particle components, wherein the determination is performed by a fitting operation, performed via the processor or logic circuit, of the measured impedance spectra to an equivalent circuit model that at least include the first electric-field-generating structure or a portion thereof.

In some embodiments, the impedance spectra is measured by applying an impedance interrogating signal having a power level and a frequency range corresponding to those associated with the control of the polarization or manipulation of the biologic or particle components (e.g., 20-200 Vpp/cm and over 0.1 MHz to 10 MHz); and measuring a resulting voltage resulting from the applied impedance interrogating signal, wherein the measured resulting voltage has an amplitude and phase properties that defines the impedance spectra.

In some embodiments, the first electric-field-generating structure comprises an electrode portion and an insulating barrier, wherein the insulating barrier corresponds to the at least one internal capacitive structure.

In some embodiments, the electrode portion is configured as at least one of a contactless dielectrophoresis electrode; a bi-polar dielectrophoresis electrode; a passivated dielectrophoresis electrode; an electrowetting on dielectric electrode; and a droplet manipulating system electrode.

In some embodiments, the impedance spectra is measured when the biologic or particle components are flowing within the microfluidic channel.

In some embodiments, the impedance spectra is measured when the microfluidic channel is filled with a test media (e.g., a high salt media) that does not have present biologic or particle components of interest.

In some embodiments, the first electric-field-generating structure is used for electrokinetic trapping (e.g., AC electrokinetic trapping), acoustic trapping, or dielectrophoresis operation, the functional quantification of at least one internal capacitive structure or the characteristic of the biologic or particle component comprising at least one of a quantification associated with efficacy of the electrokinetic trapping, acoustic trapping, or dielectrophoresis operation; a quantification associated with a frequency response of the electrokinetic trapping, acoustic trapping, or dielectrophoresis operation; a quantification of parasitic voltage drops of the first electric-field-generating structure; a quantification associated with identifying a particle type and its position in the microfluidic channel; and a quantification associated with sample transport post-trapping operation.

In some embodiments, the first electric-field-generating structure and corresponding controls are configured for a target cell type selected from the group consisting of tumor cells, immune cells, and stem cells.

In some embodiments, the first electric-field-generating structure and corresponding controls are configured for dielectrophoresis operation having a wide frequency range of at least 1 MHz (e.g., between 0.1 MHz and 10 MHz).

In some embodiments, the measured impedance spectra is used for the control of the selective polarization or manipulation of the biologic or particle components when flowing through the microfluidic channel.

In some embodiments, the measured impedance spectra is used for the geometric or functional quantification of at least one internal capacitive structure of the first electric-field-generating structure or of the microfluidic chip.

In some embodiments, the geometric or functional quantification is used to determine an initialized control setting value used in the control of the microfluidic chip (e.g., to normalize characteristics across other chips or over time).

In some embodiments, the measured impedance spectra is used for the geometric or functional quantification of at least one internal capacitive structure of the first electric-field-generating structure or the microfluidic chip as part of a quality control assessment operation of the microfluidic chip (e.g., during or post fabrication of the microfluidic chip).

In some embodiments, the measured impedance spectra is used for the geometric or functional quantification of at least one internal capacitive structure of the first electric-field-generating structure or the microfluidic chip to determine a geometry or functional feature of the first electric-field-generating structure that is optimized for maximum trapping operation.

In some embodiments, the microfluidic chip comprises a channeled structure made of a material selected from the group consisting of a polymer (e.g., cyclic olefin copolymer (COC), polymethylmethacrylate (PMMA), and polycarbonate (PC)) and a glass.

In some embodiments, the impedance spectra is measured via active electronic components located on an electronic board that is electrically coupled to the on-chip impedance sensing elements.

In some embodiments, the equivalent circuit model includes a first set of one or more impedance-associated parameters (e.g., resistive and capacitive parameters) of at least one electrode of the first electric-field-generating structure, a second set of one or more impedance-associated parameters of the microfluidic channel (e.g., resistive and capacitive parameters), and a third set of one or more impedance-associated parameters of a capacitive structure that, at least, includes the at least one internal capacitive structure of the first electric-field-generating structure.

In some embodiments, the equivalent circuit model includes a set of one or more impedance-associated parameters of the characteristic of the biologic or particle components.

In some embodiments, at least one of the first set of one or more impedance-associated parameters, the second set of one or more impedance-associated parameters, and the third set of one or more impedance-associated parameters, includes an inductive parameter.

In some embodiments, the impedance interrogating signal is applied across a probe resistor located in the microfluidic chip and electrically connected (e.g., in series or parallel) to the first electric-field-generating structure and associated structure or is applied across the first electric-field-generating structure and associated structure.

In some embodiments, the measured impedance spectra is used for control of the first electric-field-generating structure.

In some embodiments, the measured impedance spectra is used for control of a second electric-field-generating structure located upstream or downstream to the first electric-field-generating structure.

In some embodiments, the measured impedance spectra is used for open loop control.

In some embodiments, the measured impedance spectra is used for closed loop control.

In another aspect, an impedance measurement circuit is disclosed, the impedance measurement circuit being configured to couple to a microfluidic chip device (e.g., a contactless dielectrophoresis device) configured to trap cells or particles, the impedance measurement circuit being configured to perform, in part, any of the above method, wherein the impedance measurement circuit to configured to electrically interrogate and gauge efficacy or fidelity of structures of the microfluidic chip device during an assessment state without model cells or particles running therethrough.

In another aspect, an impedance measurement circuit is disclosed, the impedance measurement circuit being configured to couple to a microfluidic chip device configured to trap cells or particles (e.g., a contactless dielectrophoresis device), the impedance measurement circuit being configured to perform, in part, any of the above method, wherein the impedance measurement circuit to configured to electrically interrogate and gauge efficacy or fidelity of structures of the microfluidic chip device for on-chip monitoring of the microfluidic chip device to spatially and temporally actuate the cells or particles via electric fields produced by the microfluidic chip device.

In another aspect, a fluidic chip device (e.g., microfluidic chip device) is disclosed comprising a plurality of microfluidic channels configured to receive a sample comprising biologic or particle components, wherein the plurality of microfluidic channels includes a first microfluidic channel; a set of electrodes located in the first microfluidic channel, wherein the set of electrodes are configured to selectively polarize or manipulate the biologic or particle components when flowing through the first microfluidic channel; and an interrogation circuit coupled to the set of electrodes to measure an impedance spectra of the set of electrodes and its structures (e.g., barrier layer of the electrodes) of the set of electrodes according of any of the above method.

In some embodiments, the interrogation circuit comprises a controller configured to generate an interrogation signal; an amplifier configured to amplify the interrogation signal or a signal derived therefrom to a power level and a frequency range corresponding to those associated with a control of selective polarization or manipulation operations of biologic or particle components of interest; and a receiver configured to detect amplitude and phase components of a returned signal corresponding to the measured impedance spectra of the set of electrodes and associated structures.

In some embodiments, the controller is configured, via instructions stored in computer readable medium of the interrogation circuit, to determine and output control signals for the control of the polarization or manipulation of the biologic or particle components when flowing through the microfluidic channel.

In some embodiments, the controller is configured, via instructions stored in computer readable medium of the interrogation circuit, to determine and output geometric or functional quantification of at least one internal capacitive structure of the first electric-field-generating structure or the microfluidic chip.

In another aspect, a cytometry system is disclosed comprising the fluidic chip of any of the above apparatus.

In another aspect, an impedance phase cytometry method, comprising: quantifying, via impedance phase contrast performed by on-chip analysis, positions of multi-cell samples aggregated into a microfluidic channel; and selectively triggering downstream separation downstream to the positions based on the quantification.

In another aspect, a system is disclosed comprising a processor or logic circuit; and a memory having instructions stored thereon, wherein execution of the instructions by the processor or logic circuit, cause the processor or logic circuit to control polarization or manipulation of biologic or particle components of interest when flowing through a microfluidic channel of a fluidic chip device according to any of the above method.

In another aspect, a system is disclosed comprising a processor or logic circuit; and a memory having instructions stored thereon, wherein execution of the instructions by the processor or logic circuit, cause the processor or logic circuit to perform geometric or functional quantification of an internal capacitive structure of an electric-field-generating structure located in the microfluidic chip and used for polarization or manipulation of biologic or particle components of interest according to any of the above method.

Other aspects and features according to the example embodiments of the disclosed technology will become apparent to those of ordinary skill in the art, upon reviewing the following detailed description in conjunction with the accompanying figures.

BRIEF DESCRIPTION OF THE DRAWINGS

The skilled person in the art will understand that the drawings, described below, are for illustration purposes only.

FIG. 12 also shows in the flowchart an example method of operation for geometric or functional quantification of the at least one internal capacitive structure or of the microfluidic chip.

DETAILED DESCRIPTION

Figure 1:
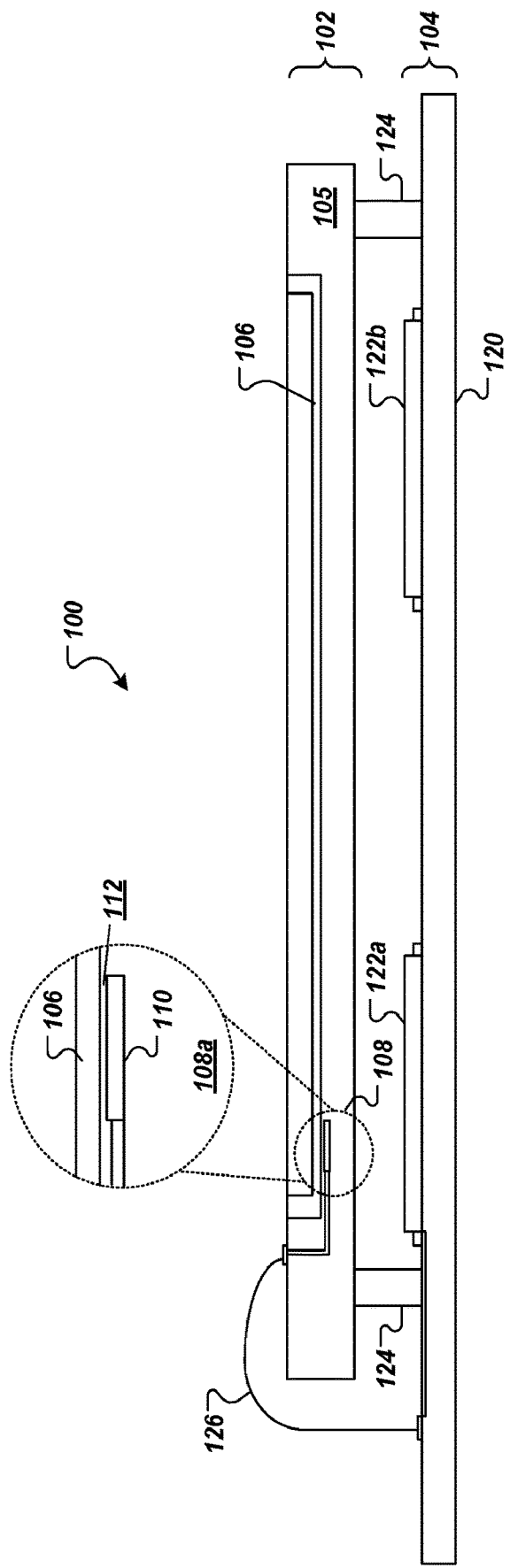
FIG. 1 shows an exemplary microfluidic chip system (e.g., a cytometry system) configured with on-chip impedance-based measurement and quantification in accordance with an illustrative embodiment.

In some aspects, the disclosed technology relates to impedance-based quantification and microfluidic control. Although example embodiments of the disclosed technology are explained in detail herein, it is to be understood that other embodiments are contemplated. Accordingly, it is not intended that the disclosed technology be limited in its scope to the details of construction and arrangement of components set forth in the following description or illustrated in the drawings. The disclosed technology is capable of other embodiments and of being practiced or carried out in various ways.

It must also be noted that, as used in the specification and the appended claims, the singular forms "a," "an" and "the" include plural referents unless the context clearly dictates otherwise. Ranges may be expressed herein as from "about" or "approximately" one particular value and/or to "about" or "approximately" another particular value. When such a range is expressed, other exemplary embodiments include from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the disclosed technology. Similarly, it is also to be understood that the mention of one or more components in a device or system does not preclude the presence of additional components or intervening components between those components expressly identified.

As discussed herein, a "subject" (or "patient") may be any applicable human, animal, or other organism, living or dead, or other biological or molecular structure or chemical environment, and may relate to particular components of the subject, for instance specific organs, tissues, or fluids of a subject, may be in a particular location of the subject, referred to herein as an "area of interest" or a "region of interest."

Some references, which may include various patents, patent applications, and publications, are cited in a reference list and discussed in the disclosure provided herein. The citation and/or discussion of such references is provided merely to clarify the description of the disclosed technology and is not an admission that any such reference is "prior art" to any aspects of the disclosed technology described herein. In terms of notation, "[1]" corresponds to the nth reference in the list. For example, [1] refers to the first reference in the list, namely 1. Jones, T. B., "Electromechanics of particles," Cambridge University Press (2005). All references cited and discussed in this specification are incorporated herein by reference in their entireties and to the same extent as if each reference was individually incorporated by reference.

In the following description, references are made to the accompanying drawings that form a part hereof and that show, by way of illustration, specific embodiments or examples. In referring to the drawings, like numerals represent like elements throughout the several figures.

FIG. 1 shows an exemplary microfluidic chip system 100 (e.g., a cytometry system) configured with on-chip impedance-based measurement and quantification in accordance with an illustrative embodiment. The exemplary microfluidic chip system 100 includes a microfluidic chip portion 102 that is coupled to an on-chip electronic circuit portion 104. As noted above, the term "on-chip" as used herein refers to a microfluidic circuit structure (e.g., microfluidic chip 102) that is mechanically and electronically integrated with electronic circuit components (e.g., electronic circuit portion 104) to form a fully integrated unit that includes all components necessary to measure and/or assess impedance spectra for the geometric or functional quantification of internal structures of the microfluidic chip and/or to measure and/or assess the impedance characteristics of the biologic or particle components to control polarization or manipulation of the biologic or particle components.

As shown in FIG. 1, the microfluidic chip portion 102 includes a substrate 105 that has formed therein a plurality of microfluidic channels 106 in which a portion or all of the channels includes one or more electric-field-generating structures 108 (see also 108a) comprising an electrode 110 and a barrier portion 112. The electrodes 110 are coupled to a corresponding electrical sources 130 (located on the electronic circuit portion 104) to each generate an electric field that can be used to selectively polarize or manipulate biologic or particle components 118 flowing within the microfluidic channel 106. The substrate 105 of the microfluidic chip portion 102 may be made of a material such as a polymer (e.g., cyclic olefin copolymer (COC), polymethylmethacrylate (PMMA), and polycarbonate (PC)) or a glass.

The electronic circuit portion 104 includes at least one circuit board 120 that houses, in some embodiments, one or more integrated circuits 122, including a peak detecting circuit and a phase detecting circuit to measure the impedance spectra of interest from the microfluidic chip portion 102. As discussed above, in some embodiments, the impedance spectra of one or more internal structures of the microfluidic chip portion 102 is measured and/or assessed. In other embodiments, the impedance spectra associated with impedance characteristics of biologic or particle components to be flowed through the microfluidic chip portion 102 is measured and/or assessed.

As shown in FIG. 1, the substrate 105 of the microfluidic chip portion 102 is mechanically linked and/or coupled to the circuit board 120 of the electronic circuit portion 104 via mechanical linkages (shown as spacers 124 and fasteners (not shown)). The electrical components (e.g., electrodes 110) of the microfluidic chip portion 102 are also electronically connected to the electrical components of the electronic circuit portion 104 over a cable 126. Of course, other mechanisms to mechanically and electrically couple the microfluidic chip portion 102 and the electronic circuit portion 104 together may be used. In some embodiments, the microfluidic chip portion 102 and the electronic circuit portion 104 are adhered to each other via adhesive. In other embodiments, the microfluidic chip portion 102 includes connectors that can mechanically and electrically couple to corresponding connectors on the electronic circuit portion 104. In some embodiments, the components of the electronic circuit portion 104 are directly mounted onto the microfluidic chip portion 102.

Application-Specific Condition Evaluation: The on-chip integration, in some embodiments, can be used to apply a high-power and high-frequency interrogation signal for the measure of impedance response of the microfluidic device at the AC power levels and frequency ranges that correspond with those used for particle manipulation, e.g., providing an interrogation signal level greater than 20 Vpp and, in some embodiments, up to 200 Vpp, and, e.g. providing a frequency output greater than 0.1 MHz and, in some embodiments, up to 10 MHz. Such interrogation and corresponding measurement is meaningful because impedance characteristics of internal structures of interest in the microfluidic chip, particularly, impedance associated with barrier capacitance and electrolyte resistance can exhibit non-linear responses as a function of applied AC voltages. Because such measurements are not available via commercially-available impedance analyzers (commercially impedance analyzers are often restricted to far lower voltage levels (<1 Vpp)), the resulting measurements is insufficient to quantify field penetration at, or near, test conditions, e.g., as would be use in real-world applications clinical or research environment.

Impedance-Based Evaluation of Device Geometry: The on-chip integration in being to provide impedance-based interrogation of device structure may facilitate the accurate measuring of the field manipulation performance of each microfluidic device without the use of valuable samples or standard dielectric particles (e.g., as use in microscopic evaluation of the microfluidic device), e.g., by enabling impedance-based quantification of field penetration and its frequency response through microfluidic insulating barrier of interest among other structures.

Impedance-Based Optimization of Device Structure: The on-chip integration in being to provide impedance-based interrogation of device structures of a microfluidic chip system may facilitate the optimization of key properties and/or design of various aspects of the microfluidic device, including, e.g., microfabricated insulating barrier (e.g., 112) as internal capacitive structures that form a part of the electric-field-generating structure 108. These properties may include, but are not limited to, thicknesses of the microfabricated insulating barrier (e.g., thickness at a thinnest or thickest portion of the microfabricated insulating barrier), surface area sizes of the microfabricated insulating barrier, surface charge property and/or distribution of the microfabricated insulating barrier, architecture features of microfabricated insulating barrier, sizes of the microfluidic channel (e.g., at the location to which the electric-field-generating structure is located), among others, including those additionally discussed herein. Indeed, the assessed properties can also be used towards maximizing field manipulation of particular micro- and/or nanoscale objects in the sample microfluidic channel.

Impedance-Based Optimization of Device Operation: The on-chip integration in being to provide impedance-based interrogation of device structures of a microfluidic chip system may facilitate the optimization of operations of the microfluidic chip, e.g., to optimize the cutoff frequency for field penetration through the barrier to ensure that the widest possible frequency range is available for selective manipulation of micro- or nanoscale objects of interest in the sample microfluidic channel. In addition to optimizing the cutoff frequency, the impedance-based measurement and evaluation may be used to optimize field penetration for enabling particle manipulation in a wide range of media conductivity under positive dielectrophoresis (particle translation towards high field) and negative dielectrophoresis (particle translation away from high field). In addition, the impedance-based measurement and evaluation may be used to optimize the levels of field penetration through the barrier to ensure manipulation of the widest possible size range of micro- or nanoscale objects in the sample microfluidic channel.

Impedance-Based Microfluidic Controls: The on-chip integration in being to provide impedance-based interrogation of the microfluidic chip may be used to quantify and determine impedance characteristics of biologic or particle components to be flowed through the microfluidic chip for purpose of polarizing and/or manipulating the biologic or particle components when flowing through the microfluidic channel or the triggering of other control mechanisms in the microfluidic chip.

Figure 2:
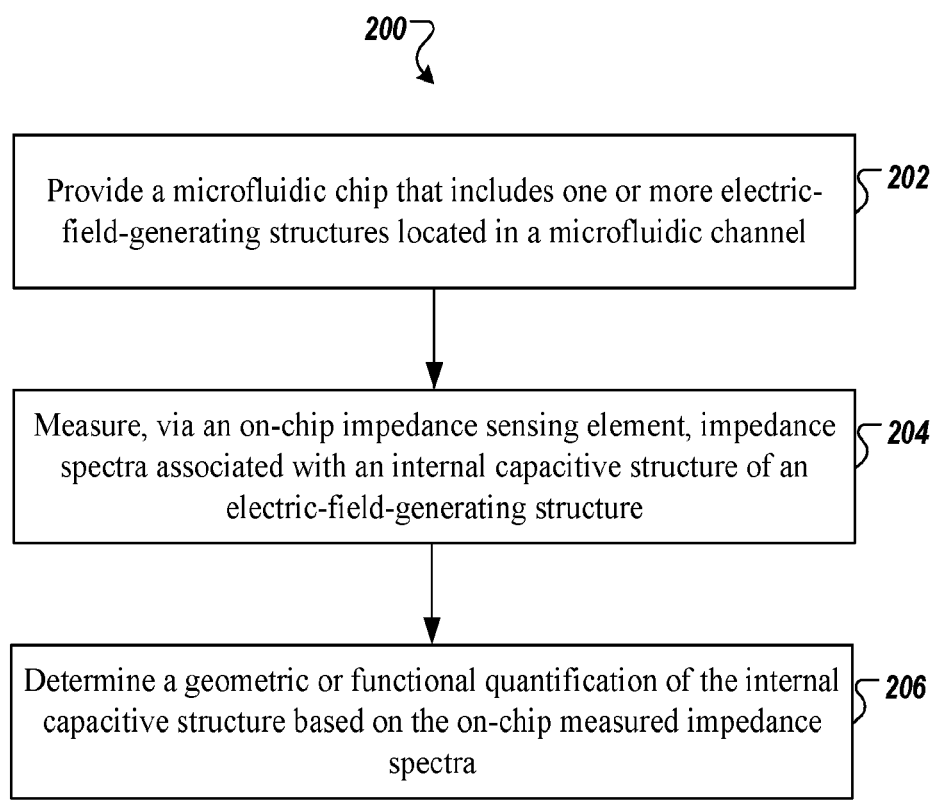
FIG. 2 shows a method to assess geometric or functional quantification of an internal capacitive structure (e.g., an electric-field-generating structure or a portion thereof) of a microfluidic chip in accordance with an illustrative embodiment.
Figure 9:
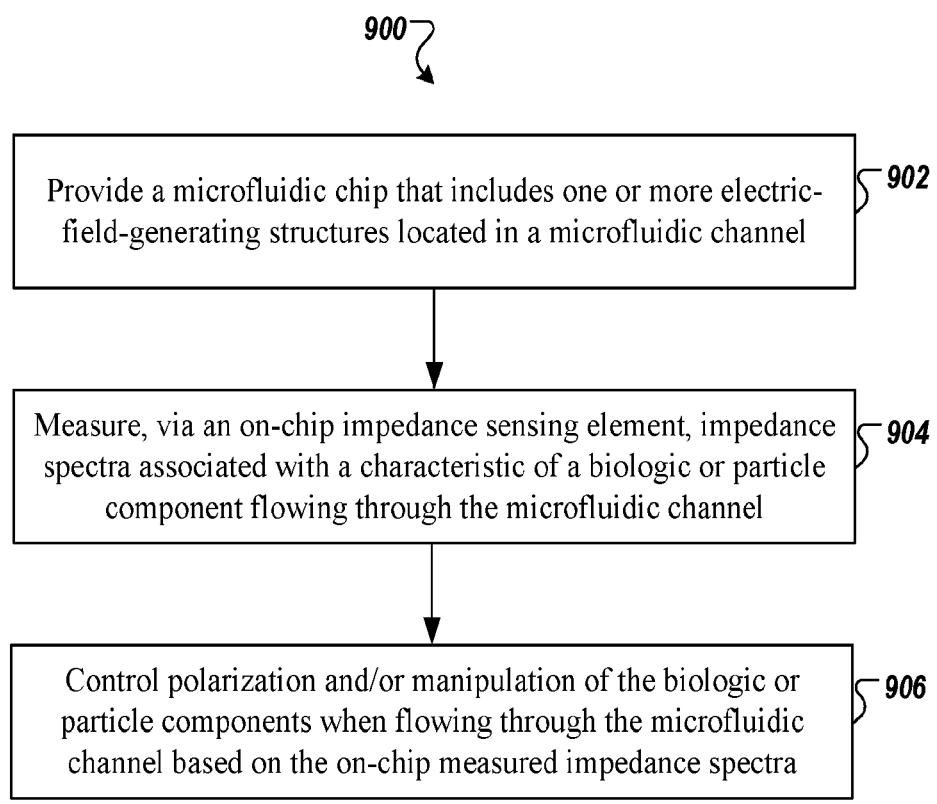
FIG. 9 shows a method to perform impedance-based control a microfluidic chip in accordance with an illustrative embodiment.

FIG. 2 shows a method 200 to assess geometric or functional quantifications of an internal capacitive structure (e.g., an electric-field-generating structure 108 or a portion thereof) of a microfluidic chip (e.g., 100) using impedance-based measurements in accordance with an illustrative embodiment. FIG. 9 shows a method 900 to perform impedance-based measurements for control of a microfluidic chip (e.g., 100) in accordance with an illustrative embodiment.

Impedance-Based Assessment and/or Quantification of Internal Structures of a Microfluidic Chip As noted above, FIG. 2 shows a method 200 to assess geometric or functional quantification of an internal capacitive structure (e.g., an electric-field-generating structure 108 or a portion thereof) of a microfluidic chip (e.g., 100) in accordance with an illustrative embodiment.

The method 200 includes providing (step 202) a microfluidic chip (e.g., 100), the microfluidic chip (e.g., 100) comprising a microfluidic channel (e.g., 106) with one or more electric-field-generating structures (e.g., 108) located therein, including a first electric-field-generating structure (e.g., electrodes and associated structure), wherein the one or more electric-field-generating structures is configured to selectively polarize or manipulate biologic or particle components flowing within the microfluidic channel.

The method 200 further includes measuring (step 204), via an on-chip impedance sensing element (e.g., on-chip resister), impedance spectra associated with at least one internal capacitive structure of the first electric-field-generating structure. In some embodiments, an interrogation signal (e.g., 130) comprising varying signal having an intensity level (e.g., greater than 20 Vpp) and/or frequency range (e.g., greater than 0.1 MHz) corresponding to an intended end-application (e.g., having at least one dielectrophoresis, contactless dielectrophoresis, electrowetting on dielectric, droplet manipulation function) is applied to an on-chip impedance sensing element 128 (see FIG. 3), e.g., a probe resister disposed on the microfluidic chip portion 102 or on the electronic circuit portion 104.

The method 200 further includes determining (step 206), by a processor, a geometric or functional quantification of the internal capacitive structure based on the on-chip measured impedance spectra. In some embodiments, the step of determining the geometric or functional quantification involves a fitting operation, performed via the processor or logic circuit, of the measured impedance spectra to an equivalent circuit model that at least include the first electric-field-generating structure or a portion thereof.

Figure 3:
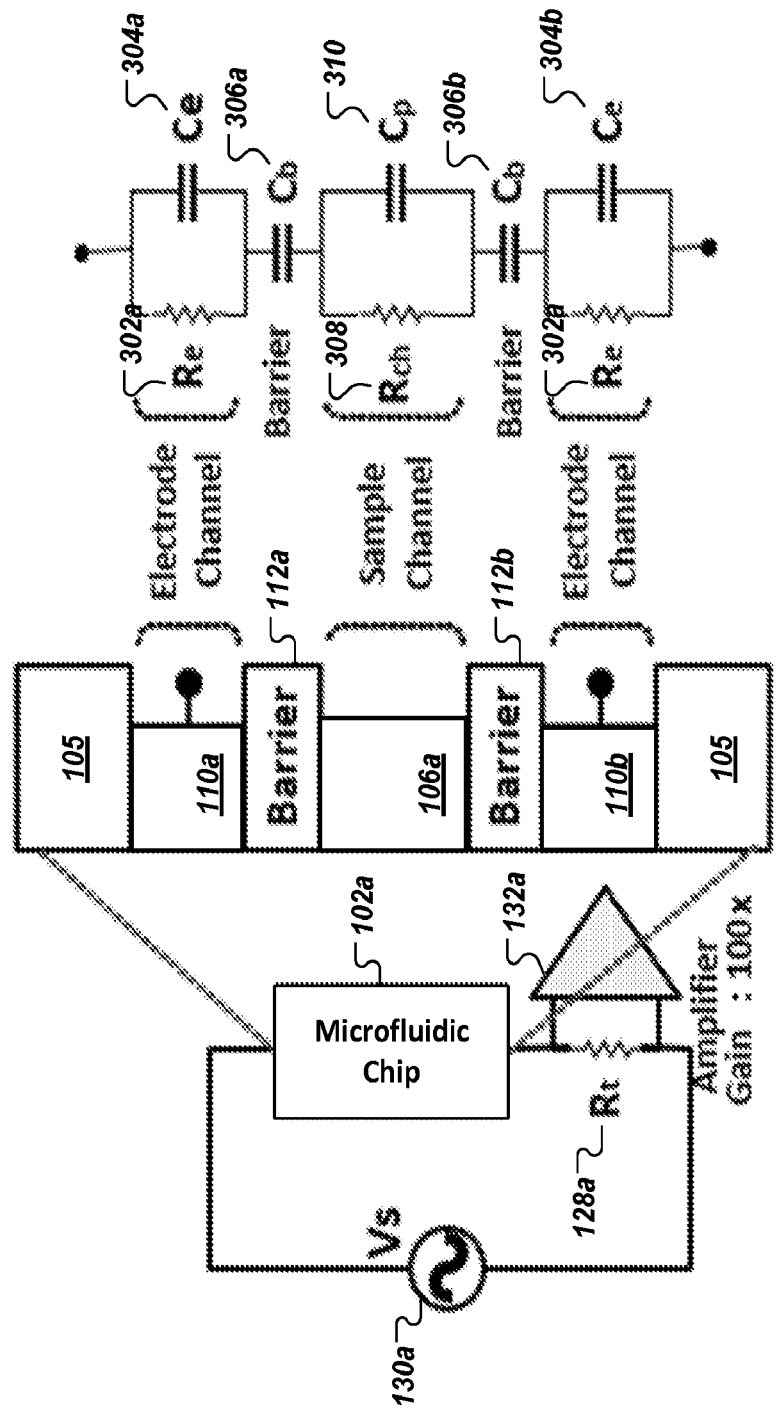
FIG. 3 shows a diagram for an exemplary microfluidic device configured to perform impedance-based assessment of geometric or functional quantification of an internal capacitive structure of a microfluidic chip in accordance with an illustrative embodiment.

FIG. 3 shows a diagram for an exemplary microfluidic device (e.g., 100) configured to perform impedance-based assessment of geometric or functional quantification of an internal capacitive structure of a microfluidic chip in accordance with an illustrative embodiment. Specifically, FIG. 3 shows a microfluidic chip portion 102 (shown as "Microfluidic Chip" 102*a*) that is electrically connected to an impedance sensing element 128 (e.g., an on-chip an impedance sensing element) (shown as a probe or test resister "$R_t$," 128*a*) to which a stimulation comprising an interrogation signal 130 (represented as a varying voltage source and shown as "$V_s$," 130*a*) is applied. Indeed, other configuration for the impedance sensing element may be used, e.g., disposing the impedance sensing element in parallel to the microfluidic chip portion 102. Referring still to FIG. 3, the probe resister $R_t$ 128*a* is coupled to an impedance measurement system 132 (e.g., an on-chip impedance measurement system) (shown as "Amplifier" 132*a*) having an associated gain (shown as "Gain: 100×"). Other gains may be used.

In FIG. 3, the microfabricated structure corresponding to an electric-field-generating structure (e.g., 108) is shown as an internal component of the microfluidic chip system 100 of interest. The electric-field-generating structure (e.g., 108) includes electrode channel structure 110 (shown as "Electrode Channel" 110*a* and 110*b*) and associated insulating barrier structure 112 (shown as "Barrier" 112*a* and 112*b*) that defines a microfluidic channel 106, or contents therein (shown as "Sample Channel"106*a*). FIG. 3 also shows an equivalent circuit/model of the microfabricated structures (e.g., 106*a*, 110*a*, 110*b*, 112*a*, 112*b*) of the electric-fieldgenerating structure (e.g., 108) in which each of the electrode channels 110a and 110b are modeled as resisters $R_e$ (302a and 302b) and capacitors $C_e$ (304a and 304b), respectively; the insulating barrier structures 112a and 112b are modeled as a capacitors $C_b$ 306a and 306b, respectively; and the microfluidic channel 106a is modeled as a resister $R_{ch}$ (308) and capacitor $C_p$ (310).

In some embodiments, the geometric or functional quantification of the internal capacitive structure includes an associated thickness of the at least one capacitive structure (e.g., thickness at a thinnest or thickest portion of the insulating barrier) (e.g., 110a, 110b, 112a, 112b corresponding to 304a, 304b, 306a, 306b). In some embodiments, the geometric or functional quantification of the internal capacitive structure includes a surface area size of the at least one internal capacitive structure (e.g., 110a, 110b, 112a, 112b corresponding to 304a, 304b, 306a, 306b). In some embodiments, the geometric or functional quantification of the internal capacitive structure includes a surface charge property of the at least one internal capacitive structure (e.g., 110a, 110b, 112a, 112b corresponding to 304a, 304b, 306a, 306b). In some embodiments, the geometric or functional quantification of the internal capacitive structure includes an architecture feature of the at least one internal capacitive structure (e.g., 106a, 110a, 110b, 112a, 112b). In some embodiments, the geometric or functional quantification of the internal capacitive structure includes a size of a portion of microfluidic channel (e.g. 106a) to which the first electric-field-generating structure is located.

Figure 4:
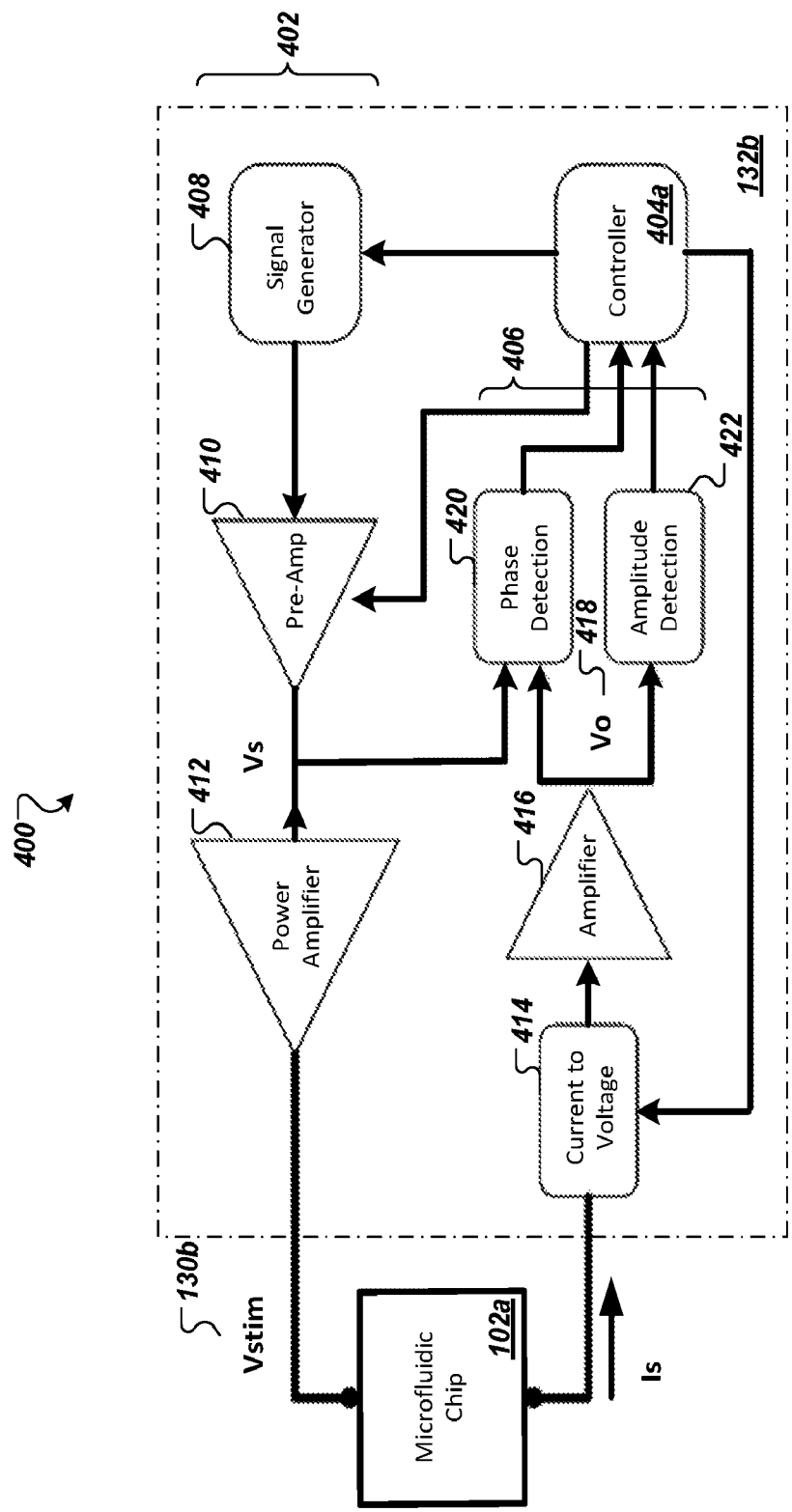
FIG. 4 shows a diagram for an exemplary an impedance measurement system (e.g., an on-chip impedance measurement system) configured to perform impedance-based assessment of geometric or functional quantification of an internal capacitive structure of a microfluidic chip in accordance with an illustrative embodiment.

FIG. 4 shows a diagram 400 for an exemplary impedance measurement system 132 (shown as 132b) (e.g., an on-chip impedance measurement system) configured to perform impedance-based assessment of geometric or functional quantification of an internal capacitive structure of a microfluidic chip 102 (shown as 102a) in accordance with an illustrative embodiment. The impedance measurement system (e.g., 132b) includes impedance measurement circuit board comprising signal generating components 402, a processing unit 404 (shown as "Controller" 404a), and impedance measuring components 406.

The signal generating components 402 are configured to generate a stimulation (e.g., a voltage stimulation) comprising an interrogation signal 130 (shown as "$V_{stim}$" 130b) and includes a signal generator 408 coupled to a pre-amplifier circuit 410 that drives a power amplifier circuit 412. The impedance measuring components 406 include a current-to-voltage conversion circuit 414 configured to receive current signal (e.g., from the probe resister 128a—not shown, see FIG. 3) to provide a voltage signal to a buffering amplifier 416 that provides output voltage 418 to a phase detection circuit 420 and amplitude detection circuit 422 that provide outputs to the controller 404a.

Amplifier Gain Flatness and Phase Shift: The signal generating components (e.g., 402), in some embodiments, are configured to generate the interrogation signal (e.g., 130b) having an amplitude/intensity sufficiently large to generate a resulting signal that can be assess by impedance measuring components 406 having a gain in the order of about 100. In this amplification range (and frequency, e.g. MHz operation), the signal generating components (e.g., 402), including the power amplifier (e.g., 412) and pre-amplifier (e.g., 410), can be configured for ideal flat gain response operation without phase lag that could affect accuracy of the measurement. The cumulative gain and phase profile may be calculated and used for error compensation in post-processing stage. An example of a pre-amplifier (e.g. 410) that may be used is the trans-impedance amplifier, model no. OPA656 (manufactured by Texas Instrument, TX), which is configured for extremely low bias current (e.g., 1 pF) for operation over a large bandwidth (e.g., up to 230 MHz). For the power amplifier stage (e.g., 412), a wideband, linear-in V/V, amplifier may be used, e.g., model no. VCA824 (manufactured by Texas Instrument, TX). The VCA824 has a 0.1 dB gain flatness up to 100 MHz (G=10) and voltage-controlled gain capability.

In other embodiments, the signal generating components (e.g., 402) may be implemented using wide-band amplifier systems as, for example, described in U.S. Patent Publication No. 2017/0218424, which is incorporated by reference herein in its entirety.

In some embodiments, the signal generating components (e.g., 402) are used to measure impedance in the fluidic device to trigger feedback within 1 ms to control electrical stimulation conditions provided by the amplifier. The controls may be based on the measured device properties, sample condition, efficacy of trapping and sample transport post-trapping.

In some embodiments, the impedance measurement may be used in conjunction with a trigger system to actively modulate the electrical stimulation provided by the amplifier, e.g., for controlling selective particle trapping, deflection or flow.

In some embodiments, the signal generating components (e.g., 402) are used measure impedance response as a means to quantify and adjust electrical stimulation to account for variations in device fidelity, such as electrical and fluidic interfacing, as well as geometry of microfabricated structures and barriers in the device.

In some embodiments, the signal generating components (e.g., 402) are used to measure impedance response for real-time quantification and amplifier field adjustment, e.g., based on alterations to the sample, including measurements to initiate sample transport into the device, media conductivity of the sample entering and leaving the device, and active flow control of sample to various regions of the device.

In some embodiments, signal generating components (e.g., 402) are used to measure impedance response for real-time quantification and amplifier field adjustment, e.g., based on the level of field manipulation performance for enabling feedback to reduce parasitic voltage drops and ensure that the widest possible frequency range is available for selective manipulation of micro- or nanoscale objects in the sample chamber.

In some embodiments, the signal generating components (e.g., 402) are used to measure local impedance response and to adjust generated electric field for controlling flow conditions of the sample.

In some embodiments, the signal generating components (e.g., 402) are used to measure local impedance response for determining viability of manipulated sample and/or to control cell viability.

In some embodiments, the signal generating components (e.g., 402) are used to measure local impedance response for adjusting stimulation conditions to the signal generating components (e.g., 402), e.g., based on determination of collection efficiency and separation purity of the sample.

Figure 5:
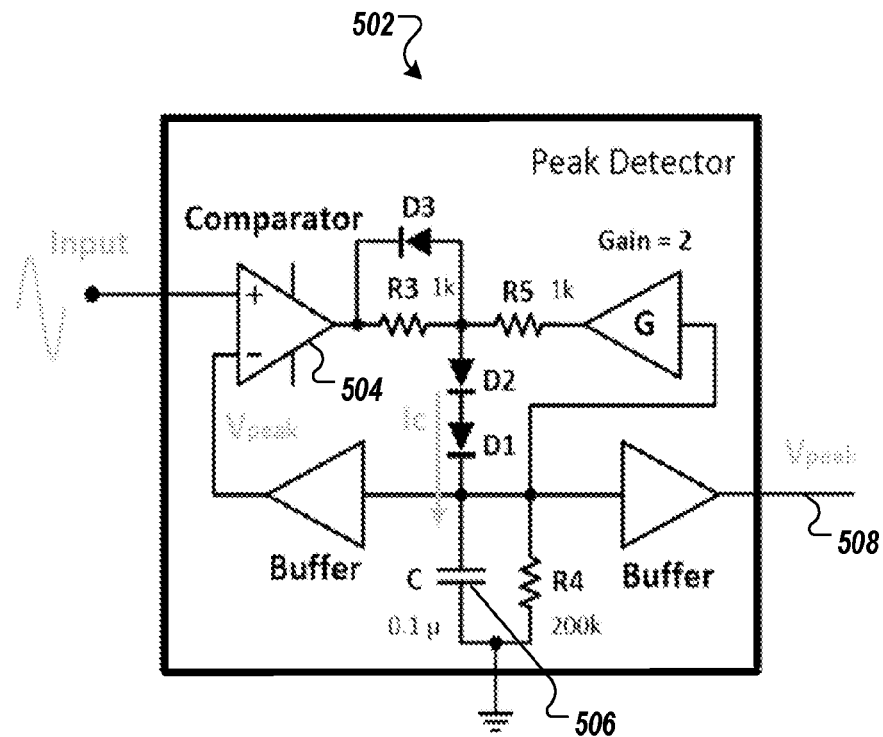
FIG. 5 shows a circuit diagram of impedance measuring components configured as a high-accuracy comparator-based detector in accordance with an illustrative embodiment.

Accurate amplitude detection: FIG. 5 shows a circuit diagram of impedance measuring components (e.g., 406) configured as a high-accuracy comparator-based detector 502 (shown as "Peak Detector" 502) in accordance with an illustrative embodiment. In FIG. 5, the comparator-based detector 502 includes a fast comparator circuit 504 (e.g., with a propagation time less than 10 ns) that is configured to charge a storage capacitor 506 to a voltage level that is as close as possible to the input peak voltage. The fast comparator circuit 504 then continuously compare the two levels to provide an output 508 that corresponds to the measured peak voltage. Further descriptions and examples of comparator-based detector are may be found in McLucas, J., "Precision peak detector uses no precision components," CAHNERS-DENVER PUBLISHING (2004). The comparator-based detector may have lower associated errors as compared to those acquired with conventional peak detection, which in some embodiments may be used, among other conventional means to assess impedance characteristics.

Figure 6:
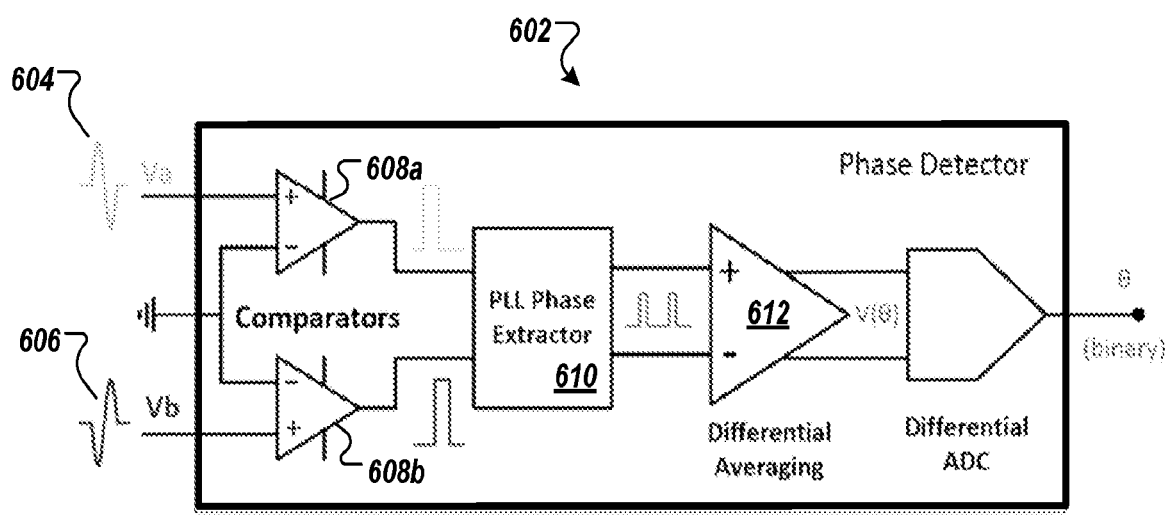
FIG. 6 shows a circuit diagram for impedance measuring components configured as a high-accuracy phase detector in accordance with an illustrative embodiment.

Accurate phase detection: FIG. 6 shows a circuit diagram for impedance measuring components (e.g., 406) configured as a high-accuracy phase detector 602 (shown as "Phase Detector" 602) in accordance with an illustrative embodiment. The phase detector 602 is configured to precisely and robustly compare the acquired and amplified signal 604 to the source signal 606 to convert them to digital streams via fast comparators (shown as 608a and 608b). The phase detector 602 includes a phase-lock-loop (PLL) circuit 610 receives the output of the comparators and provide its output an averaging filter 612 prior to converting the signal to a binary stream of the measured phase. Examples phase detection circuit includes the phase detector model no. MAX9382 (manufactured by Maxim Integrated, CA) and a high-speed amplifier model no. MAX9000 (manufactured by Maxim Integrated, CA) configured as a comparator.

In modern impedance analyzers and digital oscilloscope, the phase difference between two signals and the peak values are often calculated by comparing two arrays of data points, each corresponds to one of the input signals after being digitized using analog-to-digital converters (ADCs). Such method often requires very high-speed ADCs with sampling rates of at least 50-100 times higher than the frequency of input signals to have sufficient data points in each cycle of the signals. Additionally, the data manipulation may require implementation within a fast ASIC or FPGA. Such requirements increase the complexity and the overall cost of the design. For example, for the signal frequency of 10 MHz, the ADCs may have to be capable of sampling at a rate of 1 Giga-Hertz. Such requirements often requires in commercial impedance analyzers that very bulky and unsuitable for on-chip monitoring and triggering voltage stimulation in the mega-hertz range at 200 Vpp power levels.

Cable capacitance and total parasitic capacitance: The impedance measurement system (e.g., 132b), in some embodiments, is configured to minimize current loop area, e.g., to avoid or suppress interferences and unwanted oscillation in high-speed circuits. In some embodiments, the impedance measurement system (e.g., 132b) includes a solid ground plane under the signal routes on a PCB board and the impedance measurement system is coupled to probe resister over shielded cables.

In some embodiments, the impedance measurement system (e.g., 132b) is configured to account for parasitic capacitances in its input (e.g., of trans-impedance amplifier) along with the feedback resistor of the amplifier. This may involve measuring and/or estimation these capacitances to compensate for such associated error. Proximity of ground layers/shields to the signal lines may introduce additional sources of errors. The parasitic capacitances in the input of a trans-impedance amplifier along with the feedback resistor of the amplifier may be modeled as an RC impedance rather than a pure resistor to account for such impedance at high frequency operation (e.g., greater than 1 MHz).

Example Microfluidic Chip System

Figure 7A:
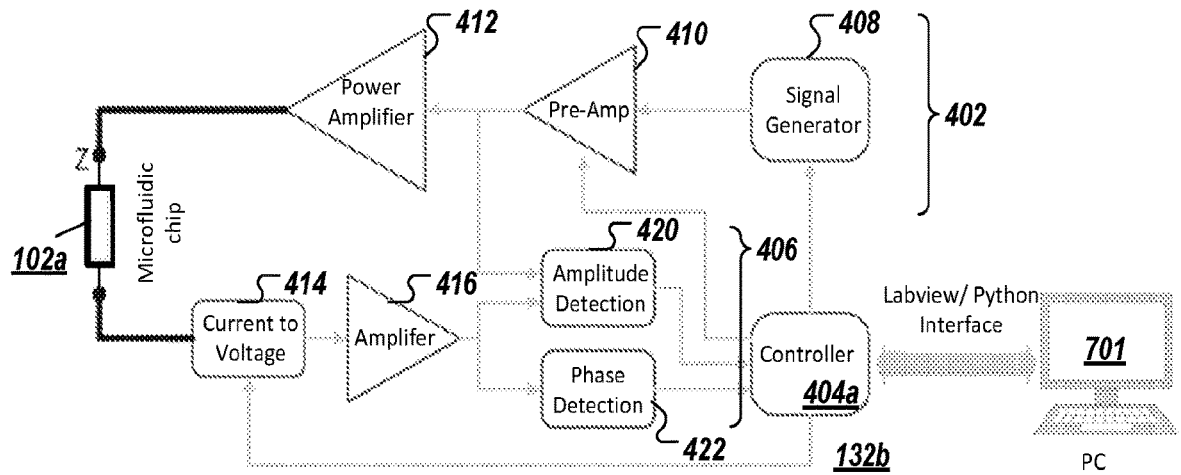
FIG. 7A is a diagram of an example microfluidic chip assessment system configured to perform impedance-based (e.g., on-chip impedance-based) geometric or functional quantification of the at least one internal capacitive structure or of the microfluidic chip in accordance with an illustrative embodiment.

FIG. 7A is a diagram of an example microfluidic chip assessment system configured to perform impedance-based (e.g., on-chip impedance-based) geometric or functional quantification of at least one internal capacitive structure or of the microfluidic chip in accordance with an illustrative embodiment. FIG. 7A includes components that perform operations as described in relation to FIG. 4. FIG. 7A further shows a second controller (shown as "PC" 701) that may provide user interface and/or data logging operations for the system.

Controller 701 may be implemented with a general-purpose or special purpose computing devices environments or configurations. Examples of well-known computing devices, environments, and/or configurations that may be suitable for use include, but are not limited to, personal computers, server computers, handheld or laptop devices, mobile phones, wearable devices, multiprocessor systems, microprocessor-based systems, network personal computers (PCs), minicomputers, mainframe computers, embedded systems, distributed computing environments that include any of the above systems or devices, and the like.

Computer-executable instructions, such as program modules, being executed by a computer may be used. Generally, program modules include routines, programs, objects, components, data structures, etc. that perform particular tasks or implement particular abstract data types. Distributed computing environments may be used where tasks are performed by remote processing devices that are linked through a communications network or other data transmission medium. In a distributed computing environment, program modules and other data may be located in both local and remote computer storage media including memory storage devices.

In its most basic configuration, computing device 701 typically includes at least one processing unit and memory. Depending on the exact configuration and type of computing device, memory may be volatile (such as random-access memory (RAM)), non-volatile (such as read-only memory (ROM), flash memory, etc.), or some combination of the two.

Computing device 701 may have additional features/functionality. For example, computing device 701 may include additional storage (removable and/or non-removable) including, but not limited to, magnetic or optical disks or tape. Such additional storage may include removable storage and/or non-removable storage.

Computing device 701 typically includes a variety of computer readable media. Computer readable media can be any available media that can be accessed by the device and includes both volatile and non-volatile media, removable and non-removable media.

Computer storage media include volatile and non-volatile, and removable and non-removable media implemented in any method or technology for storage of information such as computer readable instructions, data structures, program modules or other data. Memory, removable storage, and non-removable storage are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 1000. Any such computer storage media may be part of computing device 1000.

Computing device may contain communication connection(s) that allow the device to communicate with other devices. Computing device may also have input device(s) such as a keyboard, mouse, pen, voice input device, touch input device, etc., singly or in combination. Output device(s) such as a display, speakers, printer, vibratory mechanism, etc. may also be included singly or in combination. All these devices are well known in the art and need not be discussed at length here.

It should be understood that the various techniques described herein may be implemented in connection with hardware components or software components or, where appropriate, with a combination of both. Illustrative types of hardware components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc. The methods and apparatus of the presently disclosed subject matter, or certain aspects or portions thereof, may take the form of program code (i.e., instructions) embodied in tangible media, such as floppy diskettes, CD-ROMs, hard drives, or any other machine-readable storage medium where, when the program code is loaded into and executed by a machine, such as a computer, the machine becomes an apparatus for practicing the presently disclosed subject matter.

Although exemplary implementations may refer to utilizing aspects of the presently disclosed subject matter in the context of one or more stand-alone computer systems, the subject matter is not so limited, but rather may be implemented in connection with any computing environment, such as a network or distributed computing environment. Still further, aspects of the presently disclosed subject matter may be implemented in or across a plurality of processing chips or devices, and storage may similarly be effected across a plurality of devices. Such devices might include personal computers, network servers, handheld devices, and wearable devices, for example.

Figure 7B:
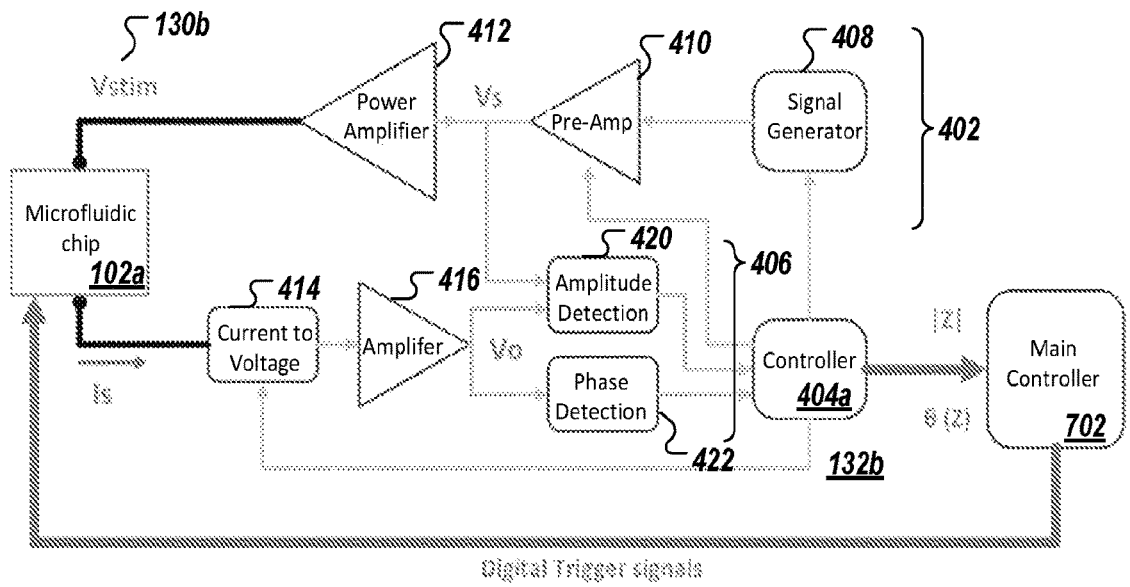
FIG. 7B is a diagram of an example microfluidic chip monitor system configured to perform impedance-based (e.g., on-chip impedance-based) control of the microfluidic chip in accordance with an illustrative embodiment.

FIG. 7B is a diagram of an example microfluidic chip monitor system configured to perform impedance-based (e.g., on-chip impedance-based) control of the microfluidic chip in accordance with an illustrative embodiment. FIG. 7B includes components that perform operations as described in relation to FIG. 4. FIG. 7B further shows a second controller (shown as "Main Controller" 702) that may provide control operation as later described herein.

Figure 8A:
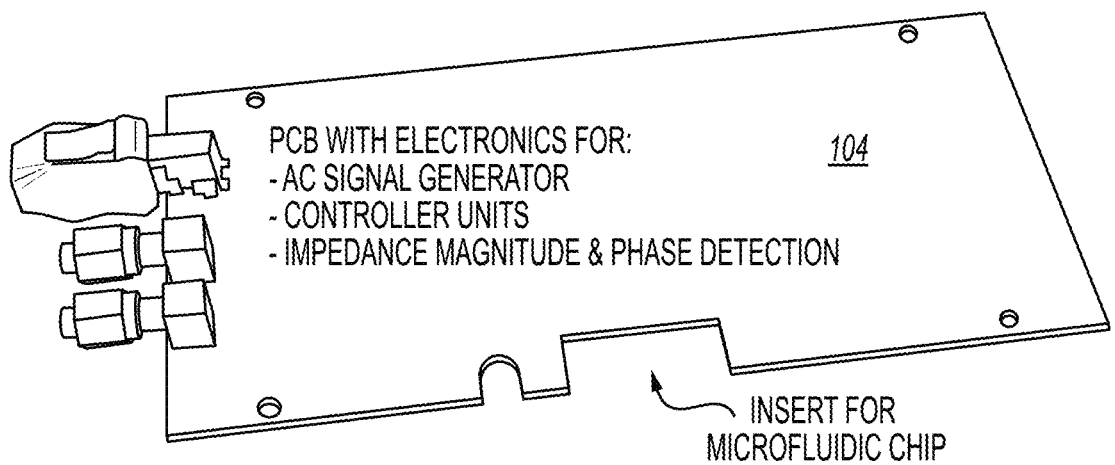
FIG. 8A shows an exemplary microfluidic chip system 100 (e.g., a cytometry system) configured with on-chip impedance-based measurement and quantification in accordance with another embodiment.

Referring back to FIG. 1, as noted above, an exemplary microfluidic chip system 100 (e.g., a cytometry system) configured with on-chip impedance-based measurement and quantification was shown. FIG. 8A shows an exemplary microfluidic chip system 100 (e.g., a cytometry system) configured with on-chip impedance-based measurement and quantification in accordance with another embodiment. In FIG. 8A, the electronic circuit portion 104 comprises a printed circuit board configured with an insert (shown as "Insert for Microfluidic Chip") for the placement of a microfluidic chip portion 102. The electronic circuit portion 104 of FIG. 8A may include electronics for a signal generator, controller, and impedance detector, e.g., as described in relation to FIGS. 4, 7A, and 7B that can interface to electrodes on microfluidic chip.

Figure 8B:
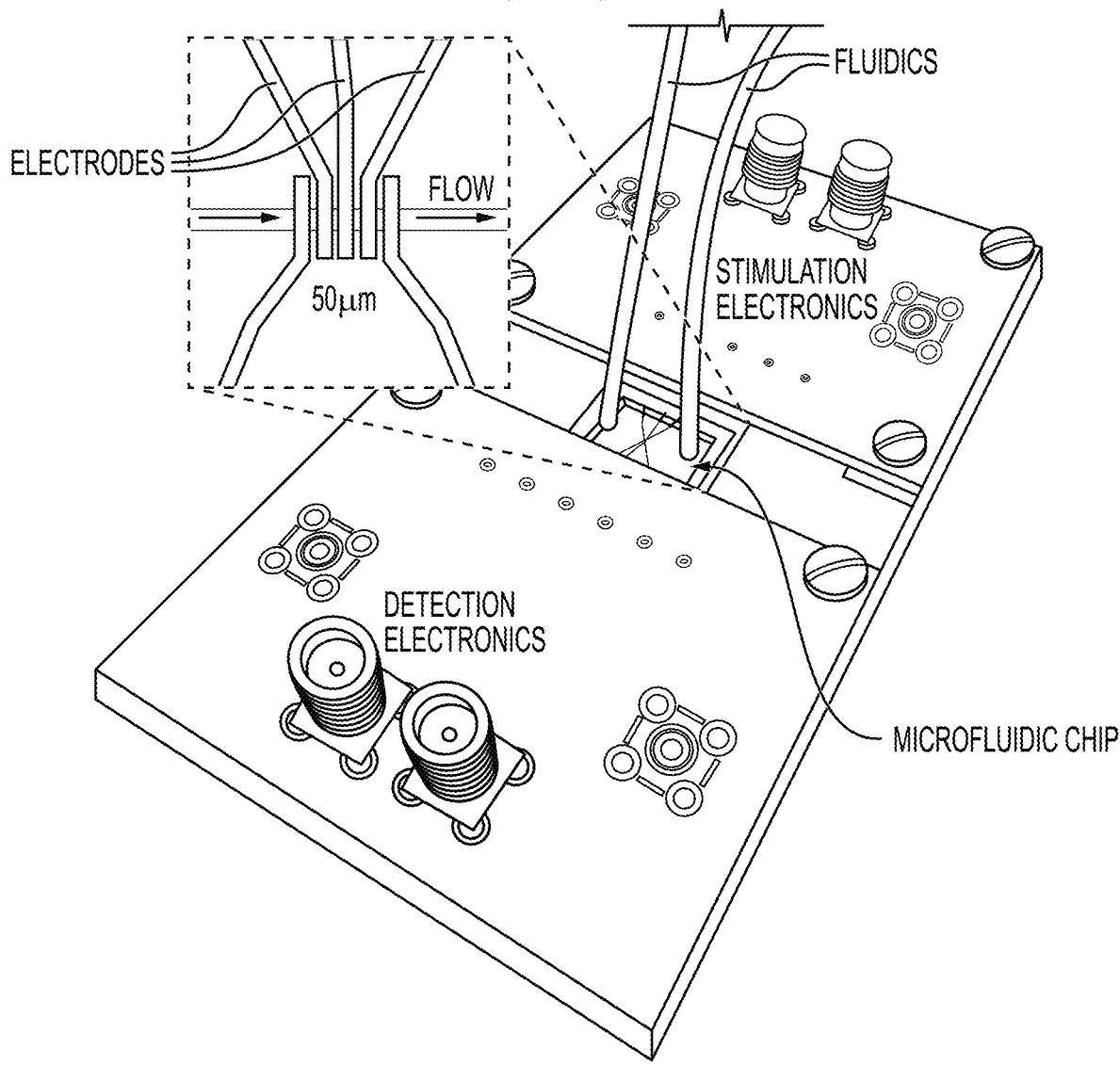
FIG. 8B shows an exemplary microfluidic chip system (e.g., a cytometry system) configured with on-chip impedance-based measurement and quantification in accordance with yet another embodiment.

FIG. 8B shows an exemplary microfluidic chip system 100 (e.g., a cytometry system) configured with on-chip impedance-based measurement and quantification in accordance with yet another embodiment. In FIG. 8B, the stimulation circuitries (e.g., 402) and the detection circuitries (e.g., comprising 404a and/or 406) are located on separate printed circuit boards that each interfaces to a microfluidic chip. The microfluidic chip of FIG. 8B is shown with electrodes patterned in a microfluidic channel.

Impedance-Based Microfluidic Controls

As noted above, FIG. 9 shows a method 900 to control (e.g., an electric-field-generating structure 108 or a portion thereof) of a microfluidic chip (e.g., 100) in accordance with an illustrative embodiment.

The method 900 includes providing (step 902) a microfluidic chip (e.g., 100), the microfluidic chip (e.g., 100) comprising a microfluidic channel (e.g., 106) with one or more electric-field-generating structures (e.g., 108) located therein, including a first electric-field-generating structure (e.g., electrodes), wherein the one or more electric-field-generating structures (e.g., 108) is configured to selectively polarize or manipulate biologic or particle components flowing within the microfluidic channel.

The method 900 further includes measuring (step 904), via an impedance sensing element (e.g., on-chip resister), impedance spectra associated with characteristics of a biological or particle component flowing through the microfluidic channel. In some embodiments, an interrogation signal (e.g., 130) comprising varying signal having an intensity level (e.g., greater than 20 Vpp) and/or frequency range (e.g., greater than 0.1 MHz) is applied that can polarize or manipulate the biologic or particle components.

In some embodiments, the interrogation signal (e.g., 130) is applied for a function selected from dielectrophoresis, contactless dielectrophoresis, electrowetting on dielectric, and droplet manipulation function. The system, in some embodiments, applies the interrogation signal to an on-chip impedance sensing element 128 (see FIG. 3), e.g., a probe resister disposed on the microfluidic chip portion 102 or on the electronic circuit portion 104.

The method 900 further includes controlling the polarization and/or manipulation of the biologic or particle components flowing through the microfluidic channel based on the on-chip measured impedance spectra.

Impedance-Based Controls Based on Characterization of Solution or Media

Figure 10:
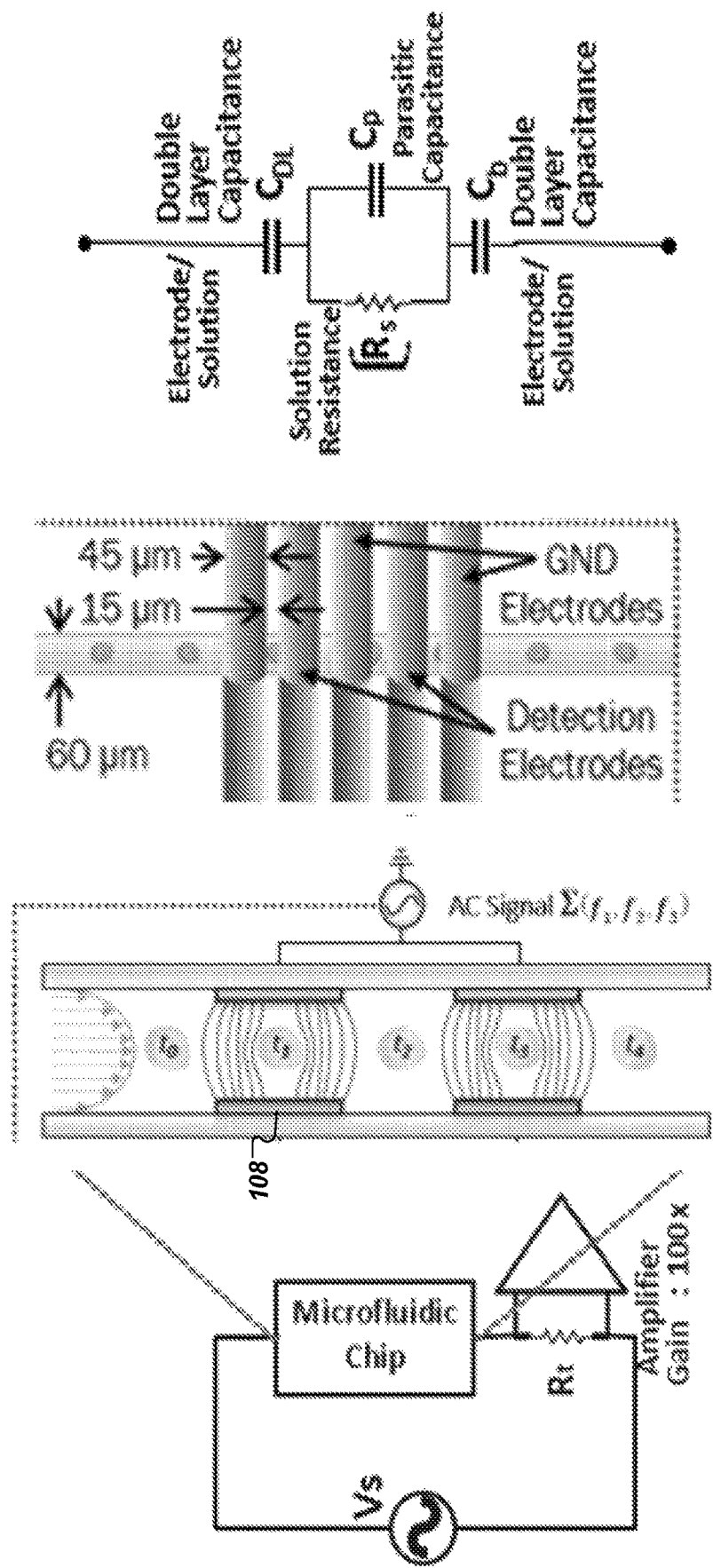
FIG. 10 shows a diagram for an exemplary microfluidic device configured to perform impedance-based control of a microfluidic chip in accordance with an illustrative embodiment.

FIG. 10 shows a diagram for an exemplary microfluidic device (e.g., 100) configured to perform impedance-based control of a microfluidic chip (e.g., by characterizing solution or media resistance in localized regions in a microfluidic channel) in accordance with an illustrative embodiment. Similar to description of FIG. 3, FIG. 10 shows a microfluidic chip portion 102 (shown as "Microfluidic Chip") that is electrically connected to an impedance sensing element (e.g., 128) (e.g., an on-chip an impedance sensing element) (shown as a probe or test resister "$R_t$") to which a stimulation comprising an interrogation signal 130 (represented as a varying voltage source and shown as "$V_s$" 130a) is applied. Indeed, other configuration for the impedance sensing element may be used, e.g., disposing the impedance sensing element in parallel to the microfluidic chip portion (e.g., 102). Referring still to FIG. 10, the probe resister $R_t$ is coupled to an impedance measurement system (e.g., an on-chip impedance measurement system) (shown as "Amplifier") having an associated gain (shown as "Gain: 100×").

In FIG. 10, the microfabricated structure corresponding to an electric-field-generating structure (e.g., 108) is shown part of a microfluidic channel in which a particle or cell is flowing (shown at position "$t_0$", "$t_1$", "$t_2$", "$t_3$", and "$t_4$"), e.g., while being measured for impedance-based control. As shown in FIG. 10, as the particle or cell flows through the microfluidic channel, it is subjected to a controllable electric field generated by the electric-field-generating structure (e.g., 108). FIG. 10 further shows a top view of respective electrodes 110 (comprising ground electrodes and detection electrodes) and example configurations and dimensions of an example microfluidic channel.

Rather than a model of the structures of the electric-field-generating structure (e.g., as discussed in relation to FIG. 3), FIG. 10 shows an equivalent circuit/model that can be used to characterize solution or media resistance ($R_s$) in localized regions of the microfluidic channel. The equivalent circuit/model may be used by a controller to adjust the controllable electric field generated by the electric-field-generating structure (e.g., 108) in real-time. It should be appreciated that conductance parameters can generally be determined from resistance parameters, and vice versa.

In FIG. 10, the equivalent circuit/model of a solution or media in the localized regions of the microfluidic channel may be modeled to include as a resistance ($R_s$) and capacitance ($C_p$) corresponding to parasitic capacitance of the solution. Additionally, the electrode and solution may be modeled as a double layer capacitance shown as $C_{DL}$ and $C_b$.

Figure 11:
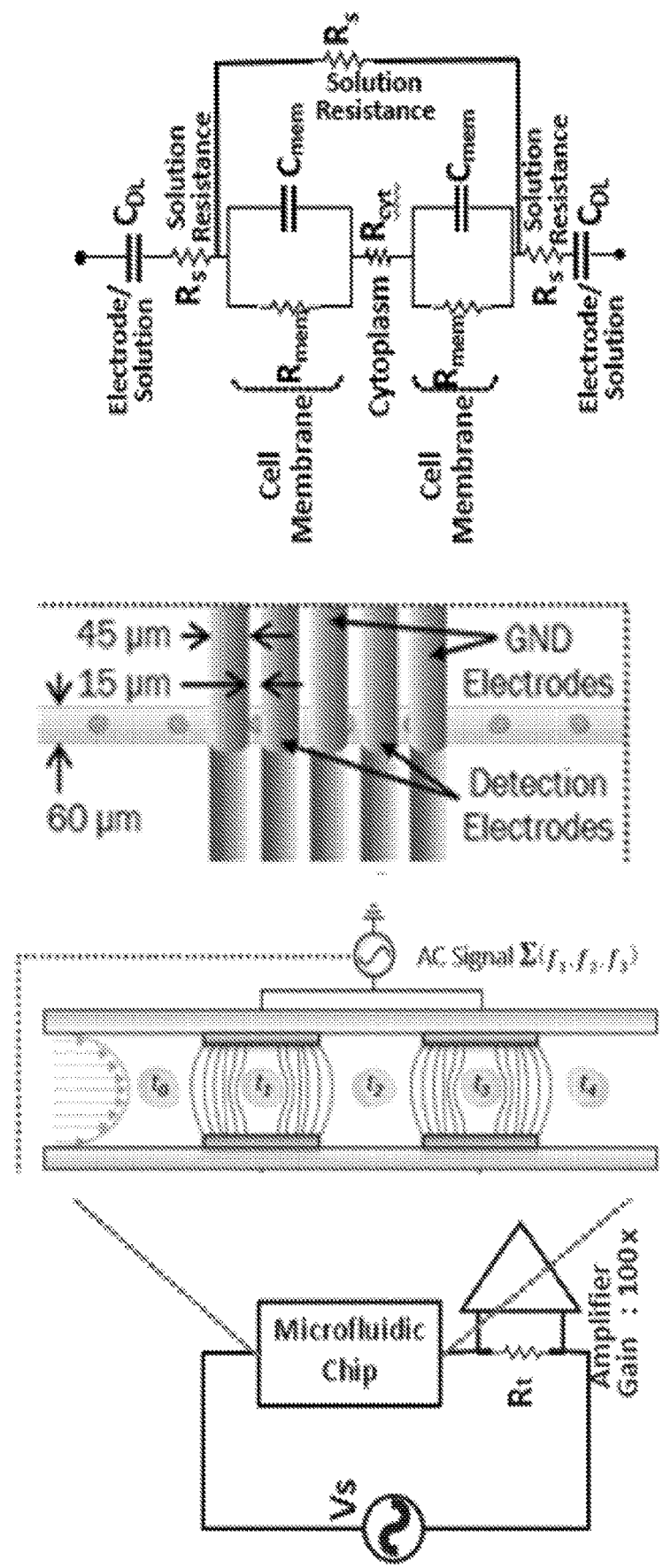
FIG. 11 shows a diagram for another exemplary microfluidic device configured to perform impedance-based control of a microfluidic chip in accordance with another illustrative embodiment.

Impedance-Based Controls to Monitor Cell Size, Membrane Capacitance, and/or Cytoplasmic Conductivity FIG. 11 shows a diagram for another exemplary microfluidic device configured to perform impedance-based control of a microfluidic chip in accordance with another illustrative embodiment. Similar to description of FIG. 3, FIG. 11 shows a microfluidic chip portion (e.g., 102) (shown as "Microfluidic Chip") that is electrically connected to an impedance sensing element (e.g., 128) (e.g., an on-chip an impedance sensing element) (shown as a probe or test resister "$R_t$") to which a stimulation comprising an interrogation signal (e.g., 130) (represented as a varying voltage source and shown as "$V_s$") is applied. Indeed, other configuration for the impedance sensing element may be used, e.g., disposing the impedance sensing element in parallel to the microfluidic chip portion 102. Referring still to FIG. 11, the probe resister $R_t$ (e.g., 128) is coupled to an impedance measurement system (e.g., 132) (e.g., an on-chip impedance measurement system) (shown as "Amplifier") having an associated gain (shown as "Gain: 100x"). In FIG. 11, the microfabricated structure corresponding to an electric-field-generating structure (e.g., 108) is shown part of a microfluidic channel in which a particle or cell is flowing (shown at position "$t_0$", "$t_1$", "$t_2$", "$t_3$", and "$t_4$". As shown in FIG. 11, as the particle or cell flows through the microfluidic channel, it is subjected to a controllable electric field generated by the electric-field-generating structure (e.g., 108).

Rather than a model of the structures of the electric-field-generating structure (e.g., as discussed in relation to FIG. 3), FIG. 11 shows an equivalent circuit/model that can be used to characterize/monitor cell size, membrane capacitance, and/or cytoplasmic conductivity for impedance-based selection. In FIG. 11, the equivalent circuit/model includes a model of the solution or media in the localized regions of the microfluidic channel, e.g., as described in relation to FIG. 10, and shown a resistance ($R_s$). The impedance corresponding to the parasitic capacitance ($C_r$) of the solution is now replaced by a model of the cell membrane comprising a resistive and capacitive parameter shown as $R_{mem}$ and $C_{mem}$ and a model of the cytoplasmic conductivity comprising a resistance ($R_{cyt}$). Additionally, similar to the model shown in FIG. 10, the electrode and solution may be modeled as a double layer capacitance shown as $C_{DL}$ and $C_b$.

The equivalent circuit/model may be used by a controller to adjust the controllable electric field generated by the electric-field-generating structure (e.g., 108) in real-time.

The models, e.g., as described in relation to FIGS. 10 and 11 may be used, to trigger and/or adjust voltage stimulation used for the polarization or manipulation of the biologic or particle components.

Referring to FIG. 7B, the controller (e.g., 404a), in some embodiments, is configured to sweep the frequency of signal generator unit (e.g., 408), e.g., from 1 KHz to 10 MHz. For example, in some embodiments, the controller is configured to sweep the frequency of signal generator unit from a first frequency to a second frequency wherein the second frequency as a max value around 9 MHz. In other embodiments, the controller is configured to sweep the frequency of signal generator unit from a first frequency to a second frequency wherein the second frequency as a max value around 8 MHz. In other embodiments, the controller is configured to sweep the frequency of signal generator unit from a first frequency to a second frequency wherein the second frequency as a max value around 7 MHz. In other embodiments, the controller is configured to sweep the frequency of signal generator unit from a first frequency to a second frequency wherein the second frequency as a max value around 6 MHz. In other embodiments, the controller is configured to sweep the frequency of signal generator unit from a first frequency to a second frequency wherein the second frequency as a max value around 5 MHz. In other embodiments, the controller is configured to sweep the frequency of signal generator unit from a first frequency to a second frequency wherein the second frequency as a max value around 4 MHz. In other embodiments, the controller is configured to sweep the frequency of signal generator unit from a first frequency to a second frequency wherein the second frequency as a max value around 3 MHz. In other embodiments, the controller is configured to sweep the frequency of signal generator unit from a first frequency to a second frequency wherein the second frequency as a max value around 2 MHz. In other embodiments, the controller is configured to sweep the frequency of signal generator unit from a first frequency to a second frequency wherein the second frequency as a max value around 1 MHz.

In some embodiments, the controller is configured to sweep the frequency of signal generator unit from a first frequency to a second frequency wherein the first frequency as a starting value around 2 KHz. In other embodiments, the controller is configured to sweep the frequency of signal generator unit from a first frequency to a second frequency wherein the first frequency as a starting value around 5 KHz. In other embodiments, the controller is configured to sweep the frequency of signal generator unit from a first frequency to a second frequency wherein the first frequency as a starting value around 10 KHz. In other embodiments, the controller is configured to sweep the frequency of signal generator unit from a first frequency to a second frequency wherein the first frequency as a starting value around 20 KHz. In other embodiments, the controller is configured to sweep the frequency of signal generator unit from a first frequency to a second frequency wherein the first frequency as a starting value around 50 KHz. In other embodiments, the controller is configured to sweep the frequency of signal generator unit from a first frequency to a second frequency wherein the first frequency as a starting value around 100 KHz. In other embodiments, the controller is configured to sweep the frequency of signal generator unit from a first frequency to a second frequency wherein the first frequency as a starting value around 200 KHz. In other embodiments, the controller is configured to sweep the frequency of signal generator unit from a first frequency to a second frequency wherein the first frequency as a starting value around 500

KHz. In other embodiments, the controller is configured to sweep the frequency of signal generator unit from a first frequency to a second frequency wherein the first frequency as a starting value around 1 MHz.

The output amplitude of the signal generator (e.g., 408) is then amplified through the pre-amp (e.g., 410) (e.g., configured with adjustable gain) and the power amplifier (eg., 412) (e.g., configured with fixed gain) units. In some embodiments, the output of power amplifier unit (e.g., 412) comprises a stimulation (e.g., 130b) having an intensity Vstim greater than 20 Vpp. In some embodiments, the power amplifier unit (e.g., 412) can generate stimulation (e.g., 130b) having an intensity Vstim up to 200 Vpp. The stimulation/control signal is applied across the fluidic chip, e.g., to the electrodes. As a result, a small AC current (Is) is generated through the fluidic chip.

The measurement portion (e.g., 406) receives the measurement of/s, and converts the received signal to an AC voltage and then amplify the signal to a level (Vo) comparable to the stimulation voltage or Vs. The phase difference between Vs and the current-to-voltage converted signal (Vo) is performed via the phase detection unit (e.g., 420). The Amplitude of Vo is also calculated using the wideband peak detection unit (e.g., 422). The results from 420 and 422 are provided to controller (e.g., 404a) for post-processing and error correction. The final output is the absolute value of Impedance (|Z|) and Phase ($\theta$(Z)), which, in FIG. 7B, is shown being provided to a main controller 702 that executes control loops for the microfluidic chip (e.g., 102a).

In other embodiments, accurate impedance analyzer is performed based on a combination of analog and logical circuits that implements ordinary differential ADC, e.g., that are integrated in a small board area (<10 sq. inches) and economic cost (<$100) (rather than high-end ADCs and processors). The system may directly interface with the microfluidic chip to provide accuracy in the phase measurement (error <±0.2°) and amplitude measurement (error <% 1). The amplitude detection may be realized using a wideband comparator-based peak detector that works in a wide amplitude range (100 mv to 8V) and wide frequency range (1 KHz to 10 MHz). FIGS. 5 and 6 show example simplified schematics of such peak detection and phase detection units.

Example Method of Operation

Figure 12:
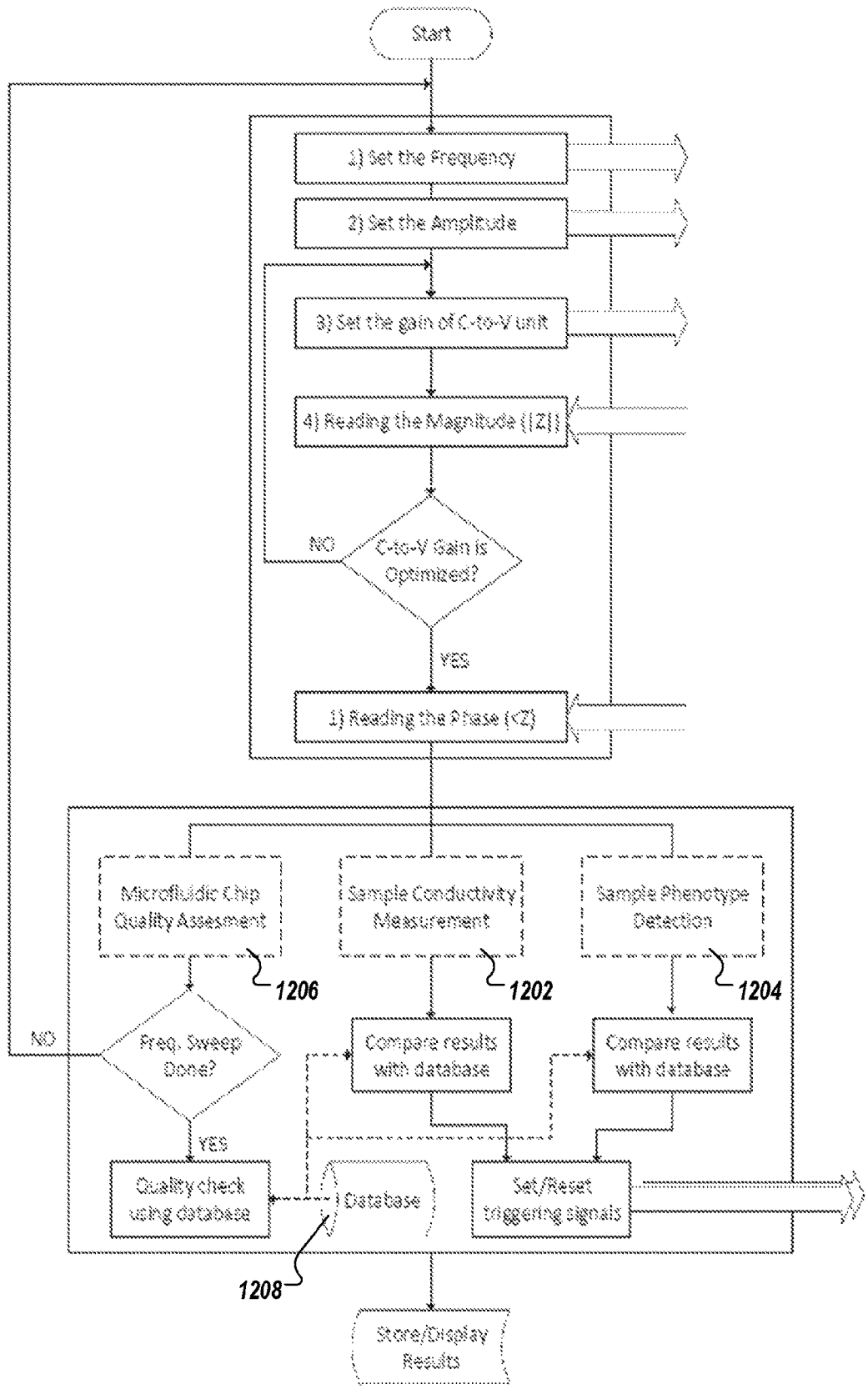
FIG. 12 shows an example flowchart illustrating methods of operation to variously control the polarization or manipulation of biologic or particle components flowing in microfluidic channels based on impedance.

FIG. 12 shows an example flowchart illustrating methods of operation (e.g., for the electronic circuit portion 104) to variously control the polarization or manipulation of biologic or particle components flowing in microfluidic channels based on impedance, for example, as described in relation to FIGS. 10 and 11 (shown as 1202 and 1204). FIG. 12 also shows in the flowchart an example method of operation (e.g., for the electronic circuit portion 104) for geometric or functional quantification of the at least one internal capacitive structure or of the microfluidic chip, for example, as described in relation to FIG. 3 (shown as 1206).

In some embodiments, the process 1202, 1204, and 1206 may be implemented together as shown in FIG. 12. In other embodiments, individual processes (e.g., 1202, 1204, or 1206) may be implemented for a given application.

In FIG. 12, the operations may be initialized to first set the frequency and amplitude setting for the signal generator (e.g., 408). The gain for the current-to-voltage unit (e.g., 414) may be set and magnitude and phase of the impedance readings may be acquired.

As shown in FIG. 12, the method of operation for geometric or functional quantification (e.g., 1206) of internal structures of microfluidic chips may be used for quality assessment of the chip. The operation may entail sweeping the frequency of signal generator unit (e.g., 408), e.g., as described in relation to FIG. 7B (or FIG. 7A). The acquired impedance spectra may be evaluated against a simulation and/or experimental results, e.g., as described in relation to the study later discussed in FIGS. 13-17 and stored in a database 1208.

As shown in FIG. 12, the method of operation for impedance-based control (e.g. 1202 and 1204) may similarly use simulation and/or experimental results, e.g., as described in relation to the study later discussed in FIGS. 13-17. The results may be used to set and reset triggering signals.

In some embodiments, the acquired impedance spectra may be acquired over time and across batches of chips to evaluate chip-to-chip variation or variations in a chip over time. The data may also be used to determine initial state to normalize characteristics, e.g., across other chips or over time.

Example Implementations and Results

Various aspects of the disclosed technology may be still more fully understood from the following description of example implementations and corresponding results and the images of FIGS. 13-21. Some experimental data are presented herein for purposes of illustration and should not be construed as limiting the scope of the disclosed technology in any way or excluding any alternative or additional embodiments.

In an aspect, an on-chip impedance method and system was developed to quantify voltage drops during DEP operation. The on-chip impedance method and system may be used for monitoring the microfluidic chip and for rapidly informing decisions on particle manipulation, as for example described herein.

To address current limitations in quantifying electric field penetration through microfluidic barriers, e.g., for determining parasitic voltage drops in microfluidic channels, a study was conducted, in part, for the purpose of optimizing electrokinetic particle manipulation. The study also addressed current limitations in enabling facile assessment of chip-to-chip variations in microfabricated geometry, without the need to use valuable biological samples or model particles. Specifically, the study developed and employed a circuit methodology capable of automated determination of the impedance frequency response of the microfluidic device under the same conditions used for particle manipulation, but without needing model particles, so that the assessed device can be used directly for downstream cell separation.

The circuit methodology developed in the study facilitates the measurement of impedance response of a microfluidic device at the AC power levels and frequency ranges that correspond to those used for particle manipulation (20-200 Vpp over 0.1-10 MHz). Whereas commercial impedance analyzers are restricted to far lower voltage levels (e.g., few Vpp), especially in the MHz range, the study beneficially facilitate the assessment of impedance due to barrier capacitance and electrolyte resistance that can exhibit non-linear responses versus applied AC voltage. The non-linear response can arise from the non-uniform spatial distribution of charges at each electrode to barrier interface, which can prevent the accurate quantification of field penetration at voltages resembling sample manipulation conditions.

In addition, the study employs the application of the impedance response to assess and optimize key properties of the microfabricated electrode configuration as well as the insulating barrier, such as its thickness, surface area and its surface charge distribution. Such optimization and resulting microfabricated electrode can to ensure that a significant fraction of the applied voltage is available for manipulation of the biological sample over the widest possible frequency range and media conductivity. This is significant since the study thus provides a field penetration that is not limited by impedances at the interfaces of the microfabricated device, but rather that the respective cut-off frequencies are adjusted based on the device architecture to enable particle manipulation by positive or negative dielectrophoresis (pDEP or nDEP) over the widest possible frequency range and media conductivity.

In addition, the study provided a circuit that can be used routinely for quality assurance of electrokinetic microfluidic devices. The circuit has a low cost and high portability. Such circuit and methodology can be used to assess fidelity of microfluidic-device geometries, e.g., for optimizing electrokinetic and piezoelectric acoustic trapping.

Figure 13:
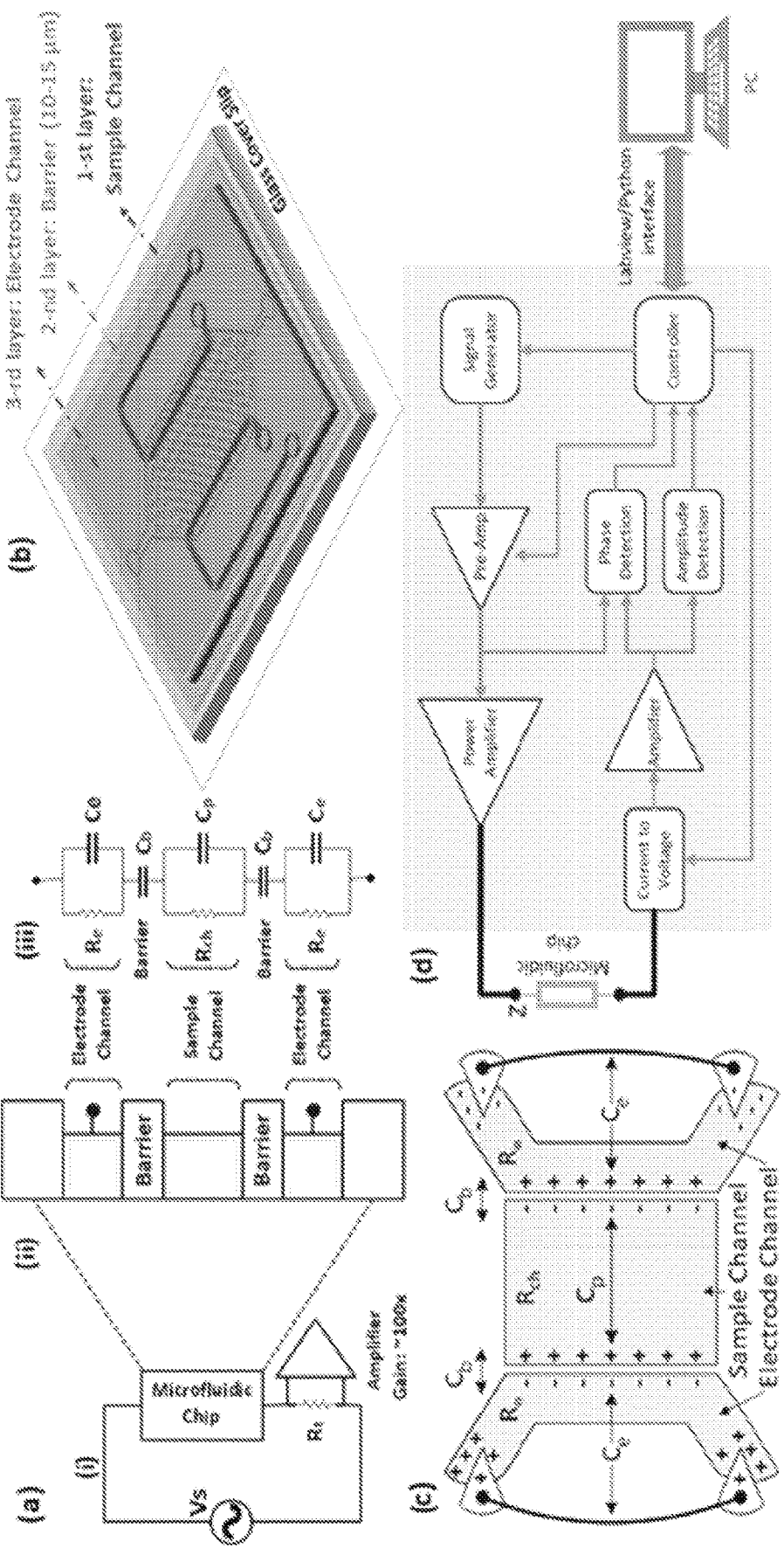
FIG. 13 comprising sub-panes (a)-(d), hereinafter referred to as FIGS. 13A, 13B, 13C, and 13D, shows various aspects of the conducted study to evaluate on-chip impedance-based evaluation of a microfluidic device in accordance with an illustrative embodiment.

FIG. 13 comprising sub-panes (a)-(d), hereinafter referred to as FIGS. 13A, 13B, 13C, and 13D, shows various aspects of the conducted study to evaluate on-chip impedance-based evaluation of a microfluidic device in accordance with an illustrative embodiment.

FIG. 13A, comprising sub-panes (i), (ii), (iii), hereinafter referred to as FIGS. 13A(i), 13A(ii), and 13A(iii), shows in FIG. 13A(i), an impedance-based measurement circuit used in the study in accordance with an illustrative embodiment. In FIG. 13A(i), the generalized set-up is shown to measure the impedance response of an electrically functional microfluidic device under the applied AC voltage (Vs) over a wide frequency range. The measurement is made based on a voltage drop measured across a fixed test resistor ($R_t$).

FIG. 13A(ii) shows a cross-section view of microfluidic chip with electrode and sample channels used in the study in accordance with an illustrative embodiment. In FIG. 13A (ii), the microfluidic chip is configured for particle manipulation by contactless dielectrophoresis in which an electric field is applied across the conductive electrode chambers that contain a high salt media (10× PBS of ~15 S/m) and the field lines penetrate across each insulator barrier into the sample chamber for the purpose of manipulating the micro- or nano-scale objects of interest within media of high salt (10× PBS of ~15 S/m) or low salt (0.1× PBS of ~0.1 S/m). The generalized microfluidic design may be adapted to other situations of electric field-induced manipulation, such as insulator DEP, electrowetting on dielectric or liquid electrodes for droplet manipulation.

FIG. 13A(iii) shows a generalized electrical equivalent circuit of chip corresponding the microfluidic chip structure of FIG. 13A(iii) used in the study in accordance with an illustrative embodiment. In FIG. 13A(iii), the equivalent circuit includes resistors and capacitors for each electrode and sample microfluidic channel and a capacitance for each barrier.

FIG. 13B show an example microfluidic chip used in the study configured with an insulating barrier interface of a sample chamber (shown in a bottom layer) that aligns to two electrode-containing microfluidic channels (shown in a top layer), the first is shown on the left side and the second is shown on a right side. In FIG. 13B, the sample chamber is shown additionally containing insulating posts to create spatial field non-uniformities for dielectrophoretic particle manipulation. For impedance measurement, in the study, voltage across the probe resistor ($R_t$) (e.g., per FIG. 13A(i)) were applied at a level small enough to not significantly reduce the proportion of Vs available for electric field manipulation within the microfluidic device. Because the current levels within microfluidic devices can fall in the sub-μA regime, especially for dielectrophoresis that is usually performed within media of low conductivity to ensure significant levels of positive dielectrophoresis (pDEP), the study employed impedance measurements over a broad range of barrier properties, frequency levels and media conductivity levels in the sample channel. In the study, a resistor with a low resistance ($R_t$) was used along a wide-band amplifier with a gain (G≈100) to enhance the sensitivity for measuring the voltage drop and its frequency response. Because parasitic capacitances, e.g., due to the leads and the measurement board, may be in parallel to $R_t$, the study was designed to account for such parasitic capacitances in the measurement to prevent, or minimize inaccurate signal degradation and phase shift at higher frequencies, which may have levels comparable to impedance of the microfluidic chip of interest.

FIG. 13C shows a model used in the study of device geometry dependent parasitic capacitances and resistances that affect the voltage fraction available for particle manipulation. While the study strived to ensure that much of the applied voltage is dropped across the sample channel ($R_{ch}$), FIG. 13C shows there are device geometry dependent parasitic capacitances (e.g., $C_p$ and $C_e$) and resistances (e.g., $R_e$) that can limit the fraction of applied voltage available for electrokinetic manipulation.

FIG. 13D shows a schematic circuit of an impedance measurement circuit and system used in the study. The impedance measurement circuit is configured with signal generator, microcontroller and amplifier for measurement of impedance response of the microfluidic chip. The impedance measurement circuit was coupled to a computer executing a user interface for the measurement via Labview.

During the study, in response to a command in Labview was sent comprising a series of frequency values to the controller of the impedance measurement circuit and an impedance measurement (comprising Magnitude and Phase) was performed by the impedance measurement circuit at those frequencies. The acquired data/results were sent back to the Labview software for post-processing, e.g., to extract circuit model parameters (e.g., of FIG. 13A(iii)) of each element of the chip (e.g., of FIG. 13A(ii)). The study determined, among other things, the voltage fraction available for electrokinetic manipulation of the tested device of FIG. 13B.

Specifically, upon receiving a set of requested frequencies from the controller (FIG. 13D), the signal generator unit (FIG. 13D) generated a low-voltage sine signal of each frequency. The generated signal was amplified in a pre-amplifier unit (FIG. 13D) with a gain value specified from the controller unit (FIG. 13D). The study generated measurements using ~150 Vpp output at high frequency in the MHz range. Further description of the amplification stage is provided in [30]. The study thus evaluated impedance of the microfluidic chip of interest under test conditions that resemble those utilized for particle manipulation and over a wide frequency test range. The "Current to Voltage" unit (FIG. 13D) was configured to convert the AC current that flowed through the chip to an AC voltage signal using a transimpedance amplifier. The resulting AC voltage had typical output values in the range of tens of milli-volts. After amplification in the "Amplifier" unit (FIG. 13D), the amplitude of the AC voltage and its phase difference with respect to the original applied voltage were calculated in the "Amplitude Detection" and "Phase detection" units (FIG. 13D). The resulting measured signals was digitized and verified by the controller (FIG. 13D) and the results were further processed by other software executing on the PC.

To facilitate such impedance measurement, the study employed a number of high accuracy circuit components and design.

(1) Amplifier Gain Flatness and Phase Shift: In the study, the amplitude of the amplifier output of the measurement circuit was configured to be sufficiently large to facilitate accurate measurement by the amplitude detection unit. A minimum amplifier gain of 100 was used. Commercially-available amplifiers, including trans-impedance amplifiers, typically do not have an ideal flat gain response range and sometimes show considerable phase lag in the MHz frequency. The study calculated the cumulative gain and phase profile and compensated for errors in post-processing stages. The trans-impedance amplifier (FIG. 13D) OPA656 (manufactured by Texas Instrument, TX) was used. Among other things, it provided extremely low bias current (1 pF) for operation over a large bandwidth up to 230 MHz. For the following amplifier stage (FIG. 13D), VCA824 (manufactured by Texas Instrument, TX) was used. The amplifier had a 0.1 dB gain flatness up to 100 MHz (for a G=10) and voltage-controlled gain capability.

(2) Accurate Amplitude Detection: In the study, rather than using classic peak detectors[31] that include a non-negligible error (~0.5V), the study used comparator-based detectors in which a fast comparator with a propagation time less than 10 ns was used to charge the storage capacitor to the level that is as close as possible to the real peak voltage. The comparator-based detectors continuously compared the two voltage levels [32]. Standard approaches for measuring amplitude of a sinusoidal signal typically involves capturing the peak of signal representing its amplitude.

(3) Accurate Phase Detection: In the study, the measurement circuit of FIG. 13D was configured to determine the phase difference between an amplified sine signal (representing the AC current) and the applied sine voltage, which is the output of pre-amplifier unit, using a precise and robust approach/circuit that compared the acquired signals using fast comparators to convert the acquired signals to digital streams. A phase detector unit that included a phase-lock-loop (PLL) circuit was used along with an averaging filter. The study did not use an analog approach to calculate the phase shift between two sine signals at the same frequency [33], which could have been limiting due to errors in amplitude detection over a wide frequency range.

To gain maximum accuracy in high frequencies (>10 MHz), in the study, both the comparators (MAX9000, Maxim Integrated, CA), and Phase detector (MAX9382, Maxim Integrated, CA) used in the measurement circuit (FIG. 13D) were selected because they were based on ECL logic family that provided performance particularly suitable for high-speed applications.

(4) Cable Capacitance and Total Parasitic Capacitance: In the study, to avoid and suppress interferences and unwanted oscillation in the high-speed circuits of the measurement circuit, the circuit and measurement scheme was designed to minimize the current loop area, which can cause parasitic inductances[34]. In the measurement circuit, a solid ground plane was implemented under signal routes on the PCB, and shielded cables were used. Because the proximity of ground layers/shields to the signal lines introduced other sources of errors, the study accounted for the parasitic capacitances in the input of trans-impedance amplifier and the feedback resistor of the amplifier as an RC impedance instead of a pure resistor. At high frequencies, impedance associated with the parasitic capacitances having both magnitude/phase differs from those of ideal resistor. The study measured and estimated these capacitances to compensate for such errors to provide a high degree of accuracy for the measurement system. The study extracted circuit model parameters and determined voltage fraction available for electrokinetic manipulation using the measurements.

Figure 14:
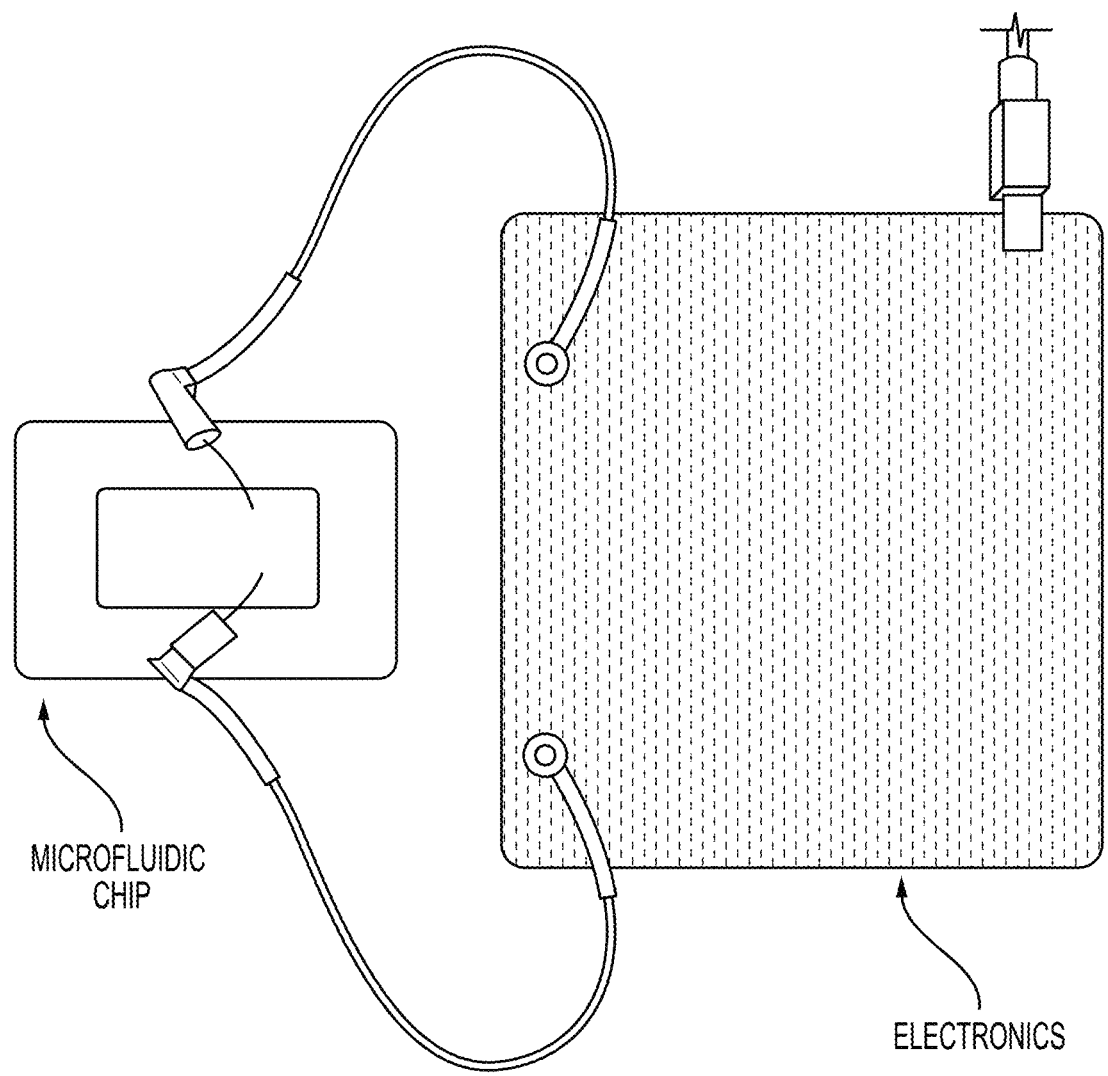
FIG. 14 shows a fabricated measurement circuit of FIG. 13D and microfluidic chip device of FIG. 13B used in the study in accordance with an illustrative embodiment.

FIG. 14 shows a fabricated measurement circuit of FIG. 13D and microfluidic chip device of FIG. 13B used in the study in accordance with an illustrative embodiment. Specifically, FIG. 14 show a printed circuit board configured measurement circuit of FIG. 13D for AC signal generation and impedance measurement that is coupled to electrodes on a microfluidic chip having the design of FIG. 13B.

Simulations: The study additionally conducted impedance-based simulations of the equivalent circuits of FIG. 13A(iii). The simulations were used to evaluate the observed impedance responses.

Results

Figure 15A:
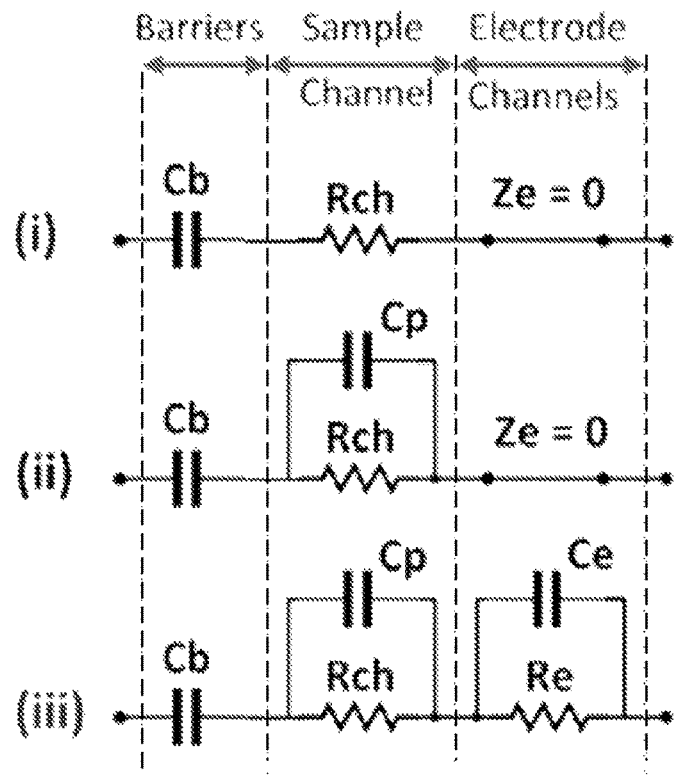
FIGS. 15A-15D shows conducted simulations and corresponding results conducted in the study in accordance with an illustrative embodiment.
Figure 15B:
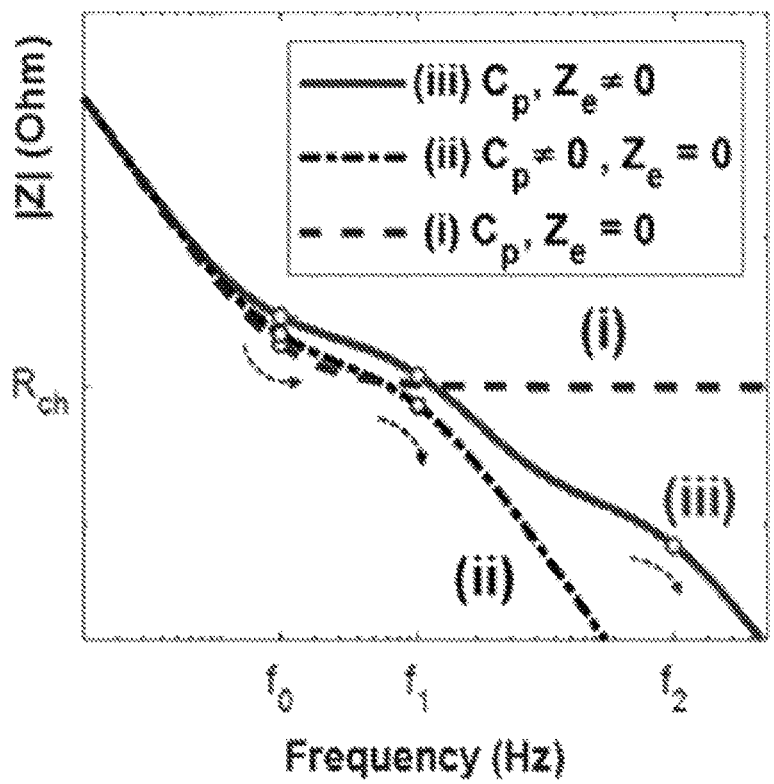
Figure 15C:
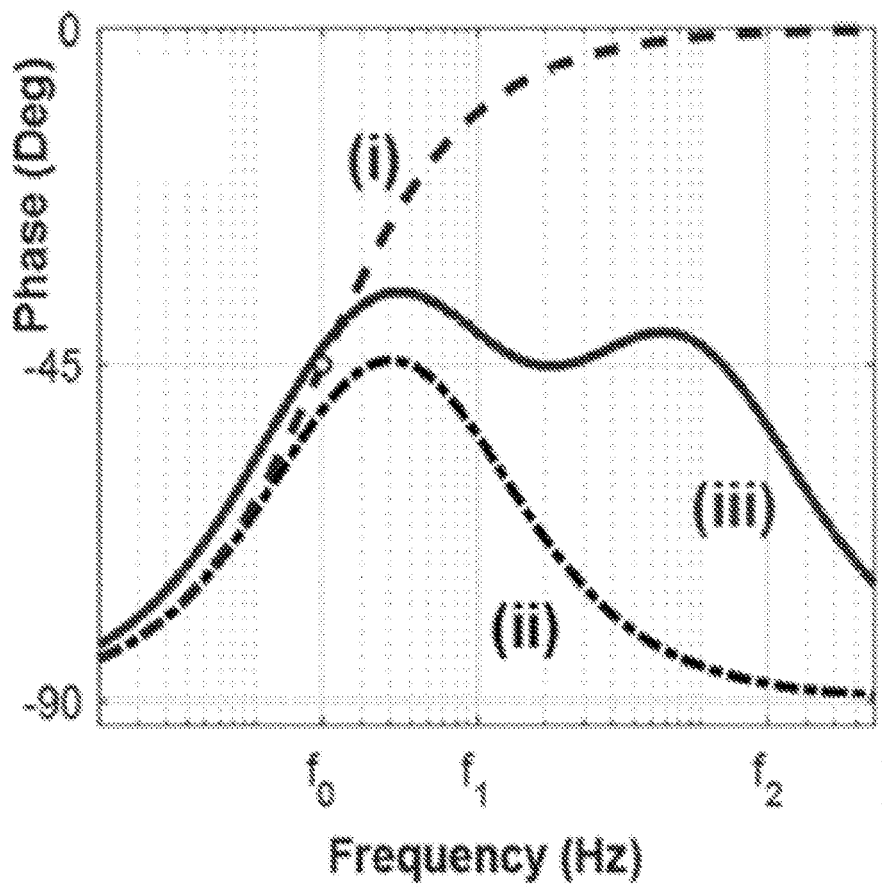
Figure 15D:
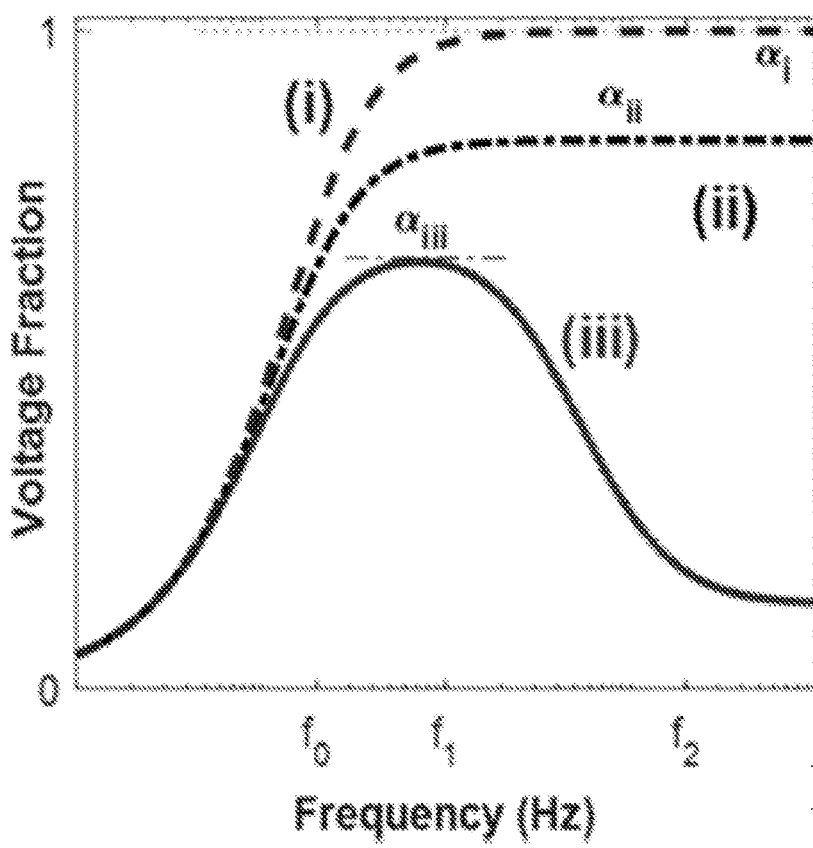
Figure 16:
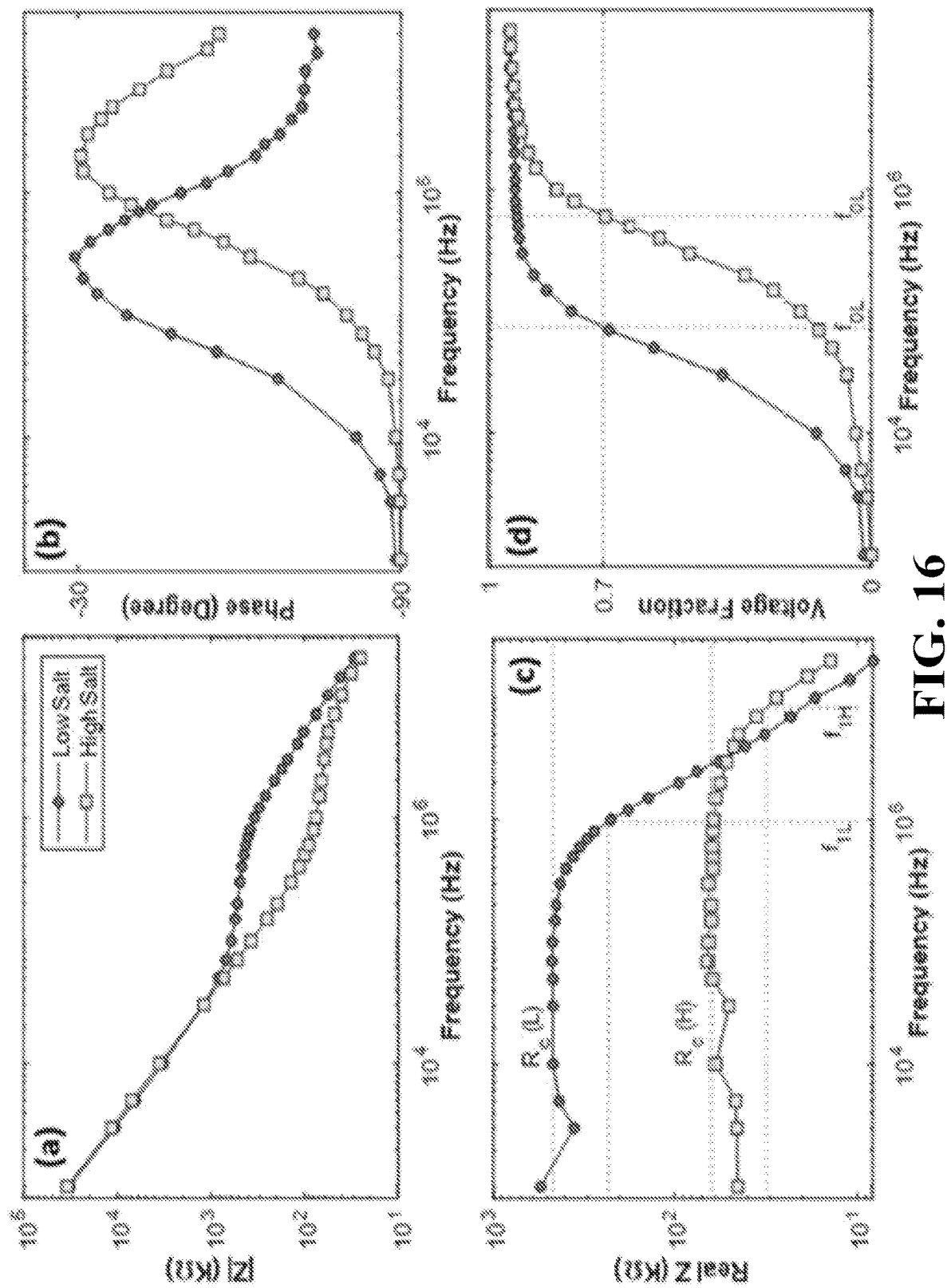
FIG. 16 comprising sub-panes (a)-(d), hereinafter referred to as FIGS. 16A, 16B, 16C, and 16D, shows experimental results of measured frequency response of microfluidic device fabricated with geometry configured for high bandwidth and high voltage fraction operation for electrokinetic manipulation in accordance with an illustrative embodiment.

FIGS. 15A-15D show conducted simulations and corresponding results conducted in the study in accordance with an illustrative embodiment. FIG. 15A, shows three equivalent circuits of the microfluidic chip device evaluated in the simulation. FIG. 15B shows simulated frequency response of the impedance magnitude of the equivalent circuits of the microfluidic chip device of FIG. 15A. FIG. 15C shows simulated frequency response of the impedance phase of the equivalent circuits of the microfluidic chip device of FIG. 15A. FIG. 15D shows simulated frequency response of the simulated voltage fraction that may be available for electrokinetic manipulation as a function of an applied voltage.

First simulated circuit ("i"): In FIG. 15A, in a first evaluated circuit ("I"), the impedance response is modeled to be chiefly determined by the net capacitance of the barriers ($C_b$) and the resistance of the sample channel ($R_{ch}$) in which dielectrophoretic manipulation is modeled to occur within a channel medium modeled with low conductivity (~0.1× PBS) while the electrode channel is modeled as a high conductivity media (10× PBS). The simulation ensured minimal impedance contribution due to resistance in the electrode channel ($R_e$). In the simulation, assuming $C_b$=~5 pF and $R_{ch}$=~500 kW, the study expected and observed that the real component of the impedance would start at a stable level at low frequencies that is driven by $R_{ch}$ and would then drop off at high frequencies. FIG. 15B shows the response of the impedance magnitude linearly dropping according to a slope corresponding to the inverse of $C_b$, and the dispersion having a single cut-off frequency ($f_0$) corresponding to the electric field penetration through $C_b$.

FIG. 15C shows the impedance phase and its transitions away from a capacitor response of 90° to 45° at the cut-off frequency. Based on these result, the study computed the voltage fraction shown as line "i" in FIG. 15D. The voltage fraction is a fraction of the applied voltage that is dropped across the sample channel and that is the available for electrokinetic manipulation. At low frequencies (e.g. beyond the cut-off frequency $f_0$), FIG. 15D shows that the voltage fraction is low when the high impedance due to dominance of $C_b$ causes the majority of the applied voltage to be dropped across the barrier, e.g., with a dispersion towards the voltage fraction of 1 beyond the cut-off frequency ($f_0$).

Second stimulated circuit ("ii"): The equivalent circuit "i" of FIG. 15A fails to accurately capture the higher frequency dispersion beyond the first cut-off frequency ($f_0$). In a second stimulation circuit ("ii"), the study evaluated parasitic capacitance in the sample channel ($C_p$) that can occur in parallel to Rai in the sample channel, as shown in equivalent circuit ("ii") of FIG. 15A. This additional capacitance ($C_p$) was observed to cause a second cut-off frequency ($f_1$), as shown in the dispersion in the line corresponding to "ii" in FIG. 15B that results in a linear drops at a corresponding slope. In FIG. 15C, the impedance phase of line "ii" is shown to exhibit another inflection towards 90° that may be attributed to the capacitive behavior. In FIG. 15D, the voltage fraction of line "ii", rather than approaching a voltage fraction value of "1", the maximum fraction is shown to be limited to less than unity by a factor determined by: ($C_b/[C_b+C_p]$).

Third stimulated circuit ("iii"): The equivalent circuit "iii" of FIG. 15A further includes input impedances in the electrode channel due to the lead-in parasitic resistance ($R_e$) and capacitance ($C_e$). In circuit ("iii"), the study expected and observed another high frequency dispersion in line "iii" of FIG. 15B corresponding to a cut-off frequency $f_2$. In FIG. 15D, a high frequency drop-off was observed, per line "iii", in the simulated voltage fraction.

Parameter Fitting: The study fitted parameters of the circuits ("i") and ("ii") of FIG. 15A to measured impedance responses to determine R and C values for each associated layer. Indeed, the determined R and C values of can be used to assess the microfabricated geometry of a given device and corresponding type.

Impedance measurements on an optimized micro-device: To ensure that the maximum fraction of applied voltage is available for electrokinetic manipulation over a wide frequency bandwidth, the study optimized the device configuration. Firstly, the device was optimized to provide higher $C_b$ (e.g., greater than ~2 pF) to enable low $f_0$ in the tens of kHz range (since DEP responses of cells can become significant onwards from this frequency level). In addition, the device was optimized to provide lower $C_p$ (e.g., ~0.2 pF) as compared to $C_b$ to ensure minimum reduction in voltage fraction from unity beyond $f_1$. In addition, the device was optimized to provide lower $R_e$ as compared to $R_{ch}$ to push the cut-off frequency $f_2$ to higher frequencies wherein DEP responses cannot be initiated (e.g., greater than 100 MHz). Based on such optimization, the study designed and microfabricated PDMS devices configured with (i) a thin insulating barrier (~10 μm) and high depth (~100 μm) to provide $C_b$ of 5 pF or greater; and (ii) an electrode channel of small length (~300 μm) and large width (50 μm) to significantly lower $R_e$ vs. $R_{ch}$.

FIG. 16A-16D shows experimental results of measured frequency response of microfluidic device fabricated with geometry configured for high bandwidth and high voltage fraction operation for electrokinetic manipulation in accordance with an illustrative embodiment. FIG. 16A shows measured impedance magnitude characteristics of the optimized microfluidic device. FIG. 16B shows measured impedance phase characteristics of the optimized microfluidic device. FIG. 16C shows measured real component of impedance characteristics of the optimized microfluidic device. FIG. 16D shows measured calculated voltage fraction available for DEP manipulation for the characteristics of the optimized microfluidic device.

To evaluate the impedance responses of such the optimized microfluidic device discussed in relation to FIG. 16A-16D, the sample channel of the device was filled with media of low salt (0.1× PBS at 0.15 S/m) and high salt (10× PBS at 15 S/m). From the experiment, it is apparent that a low salt media is preferable, since the cut-off frequency for field penetration through the barrier ($f_0$) occurs at well-below 100 kHz, thereby providing a broader frequency window for DEP manipulation of particles in the sample channel, whereas $f_0$ occurs only at ~600 kHz within high salt media, thereby limiting the frequency window for DEP manipulation. Similarly, FIG. 16D shows that the voltage fraction that determines the potential drop in the sample channel reaches a limiting value at an earlier frequency (~1 MHz) within a low salt media versus within a high salt media (~8.3 MHz). Indeed, devices with microfabricated structures that differ from this optimized configuration, such as those with a thicker insulating barrier or shallower channel depth could be readily identified based on a measured impedance response having a higher $f_0$ due to lower $C_b$. Similarly, variations in electrode channel and sample channel geometry could alter the respective parasitic impedances to affect the steady-state voltage fraction value.

Figure 17A:
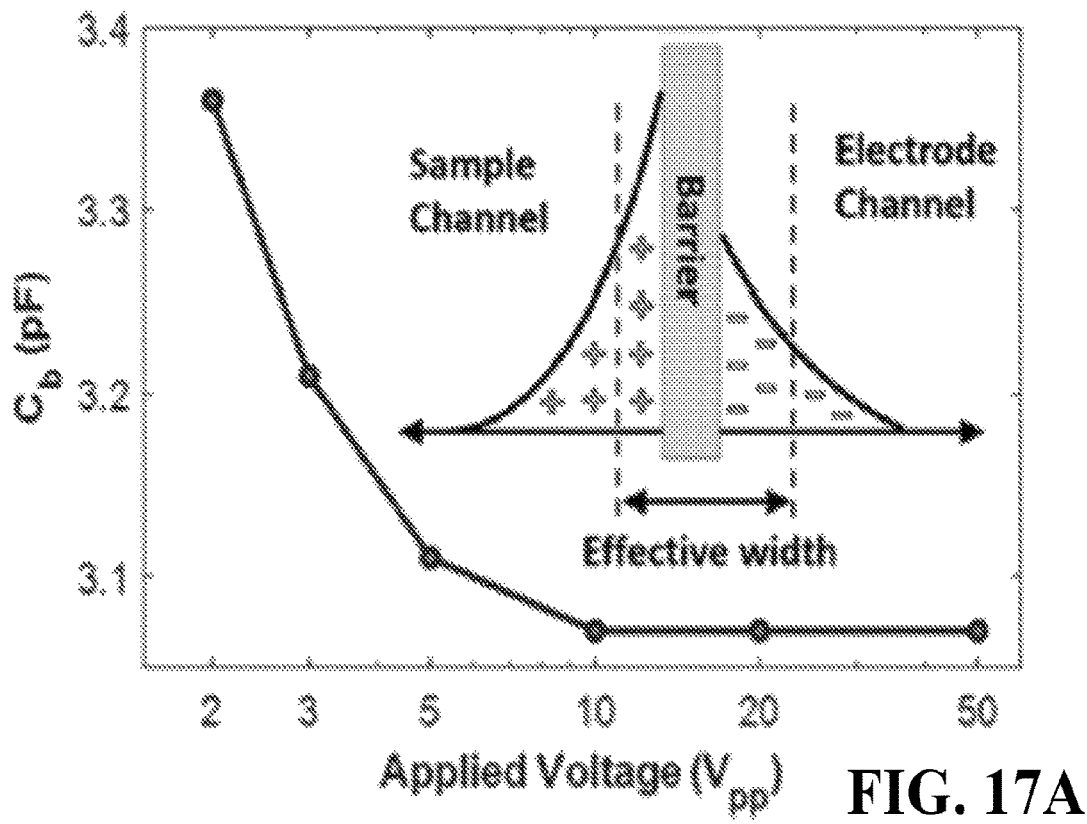
FIGS. 17A and 17B show effects of applied voltage on measured barrier capacitance and frequency response of voltage fraction for electrokinetic manipulation in accordance with an illustrative embodiment.
Figure 17B:
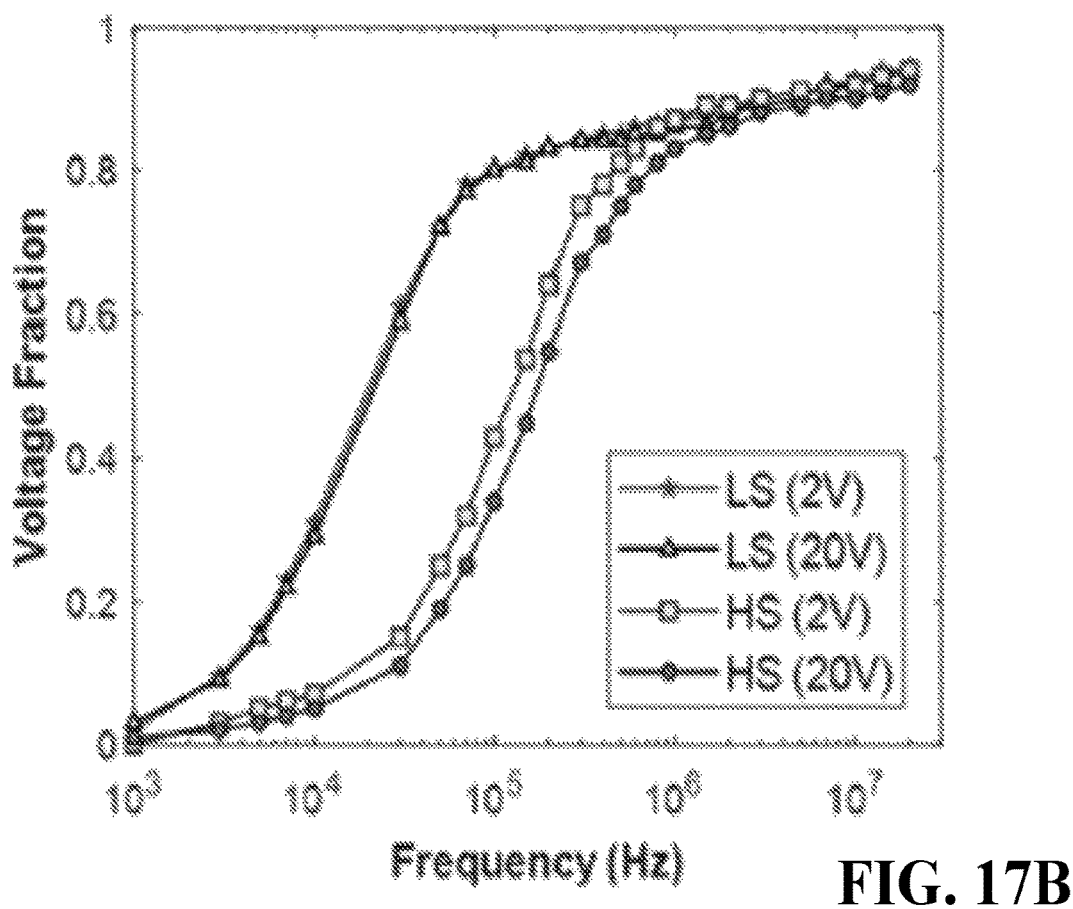

Voltage dependence of impedance response: FIGS. 17A and 17B show effects of applied voltage on measured barrier capacitance and frequency response of voltage fraction for electrokinetic manipulation in accordance with an illustrative embodiment.

FIG. 17A shows a diagram (upper right) illustrating that voltage level used to measure the impedance responses can influence the measured parameters since there is a non-uniform distribution of the space charge away from the electrolyte/barrier interface. Such non-uniform distribution can cause nonlinear capacitance and impedance behavior. FIG. 17A shows, via the plot, example non-linearity in measured capacitance versus applied voltage, and FIG. 17B shows that the non-linearity can cause an upshifting of the frequency response of the voltage fraction especially within media of high salt, due to its significantly higher levels of interfacial charge. Similar shifts can be observed in dispersions of phase and real impedance.

Assessing microfabrication fidelity based on impedance: The study further evaluated utility of the instant impedance approach and system by showing its sensitivity towards assessing devices with known microfabrication defects, such as: (1) those with misaligned layers; and (2) shadowing-related lithography error in one layer versus another to alter the sample channel width versus that of the electrode channel.

FIGS. 18A, 18B, 19A, 19B, 19C, and 19D show another aspect of the study conducted to evaluate microfabrication defects of micro-devices due to misaligned layers in accordance with an illustrative embodiment.

Figure 18A:
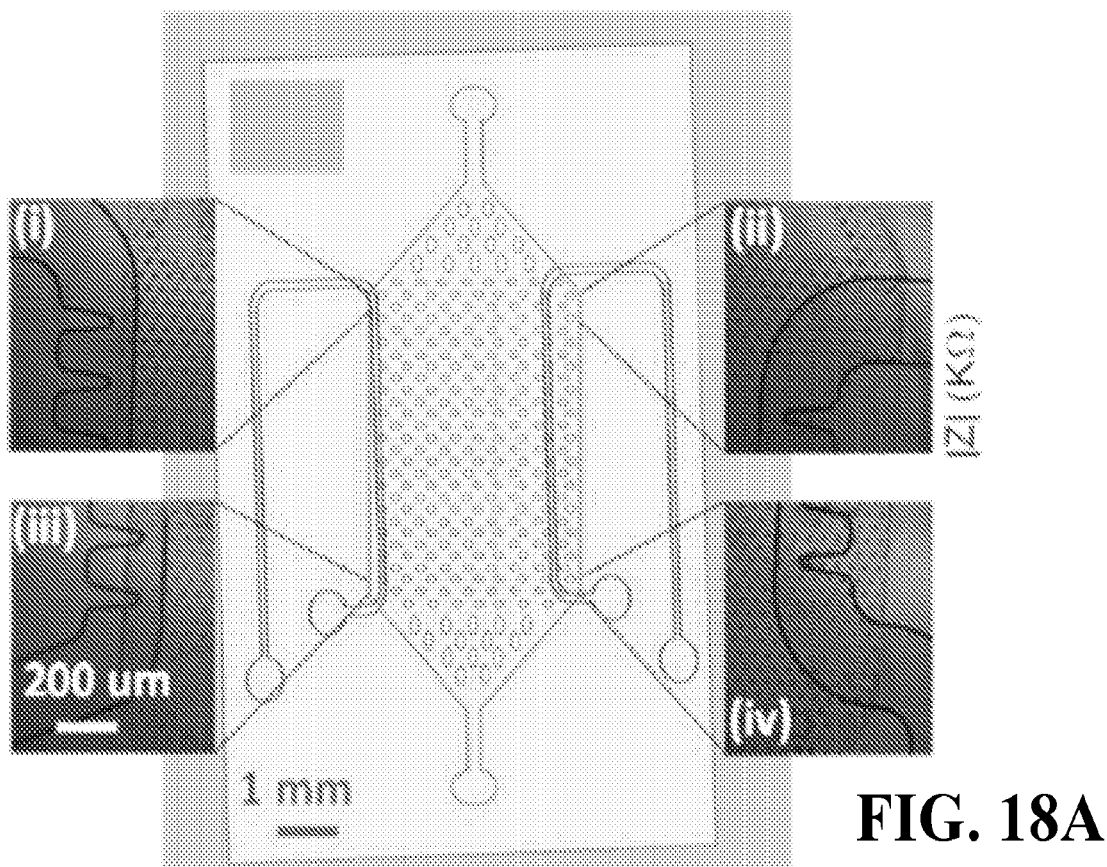
FIGS. 18A and 18B show a study conducted to evaluate microfabrication defects of micro-devices due to misaligned layers in accordance with an illustrative embodiment.
Figure 18B:
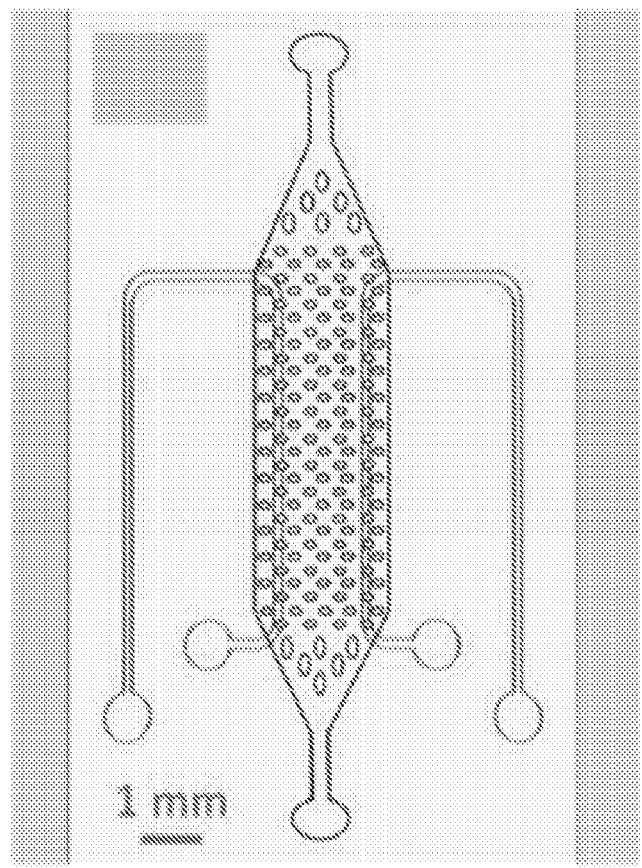
Figure 19A:
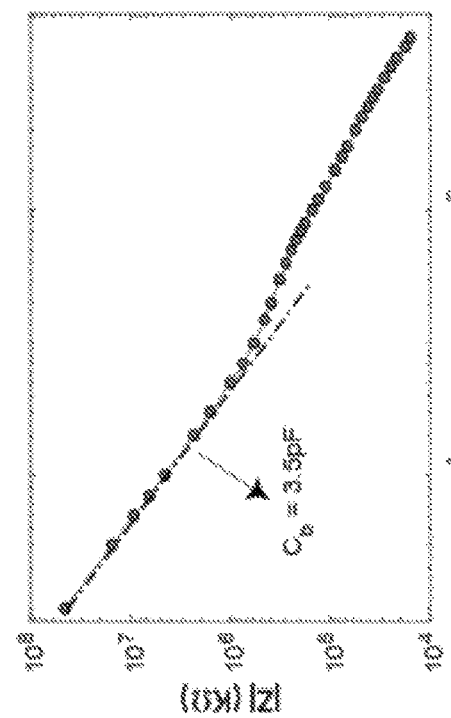
FIGS. 19A, 19B, 19C, and 19D show experimental results of impedance quantification of microfabricated devices of FIGS. 18A and 18B in accordance with an illustrative embodiment.
Figure 19B:
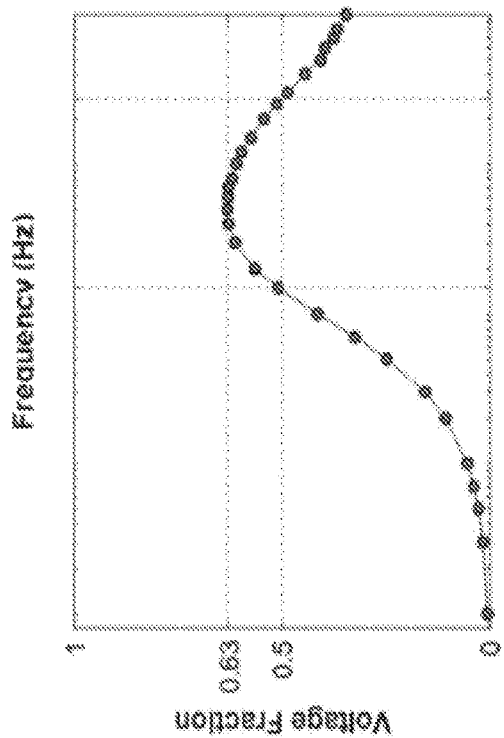
Figure 19C:
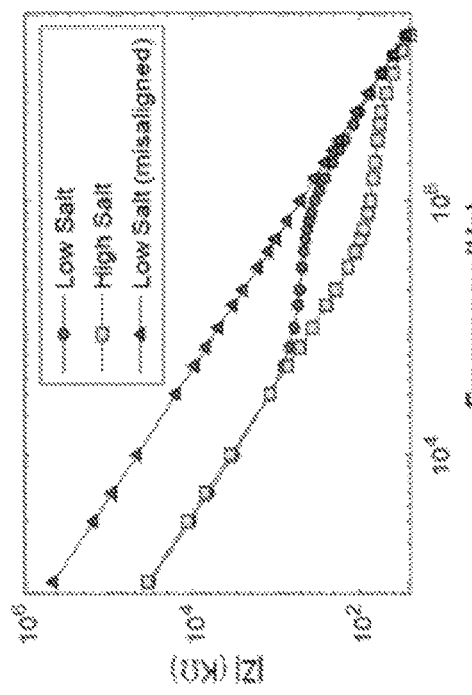
Figure 19D:
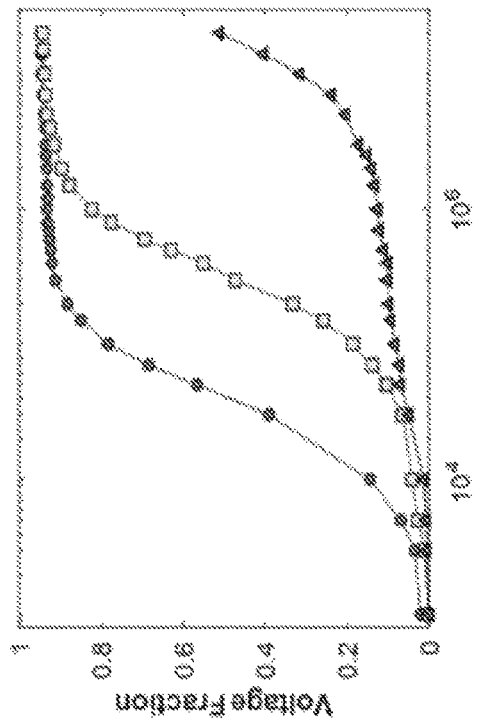

FIG. 18A shows a microfabricated device with misaligned interlayers and that interlayer misalignment alters the barrier capacitance between layers ($C_b$). FIG. 18B shows microfabricated device fabricated with lithography errors that can influence the sample channel width alter sample channel resistance ($R_{ch}$). Indeed, these defects can be quantified and identified by fitting relevant circuit parameters to impedance frequency response. FIGS. 19A, 19B, 19C, and 19D show experimental results of impedance quantification of microfabricated devices of FIGS. 18A and 18B in accordance with an illustrative embodiment. FIG. 19A shows impedance frequency response for a properly microfabricated device filled with a low salt media and with a high salt media an improperly microfabricated device that has misalignment defects. FIGS. 19C and 19D shows corresponding voltage fraction available for electrokinetic manipulation at each relevant frequency range for the respective defective devices.

In FIG. 18A, it is observed that misaligned layers can cause the barrier capacitance on one side to be lower than on the other side. Since capacitances added in series are dominated by the lower capacitance, the net capacitance of the resulting device is lowered versus a well-aligned device (e.g., whose impedance characteristics are shown in FIGS. 16A-16D).

Figure 20:
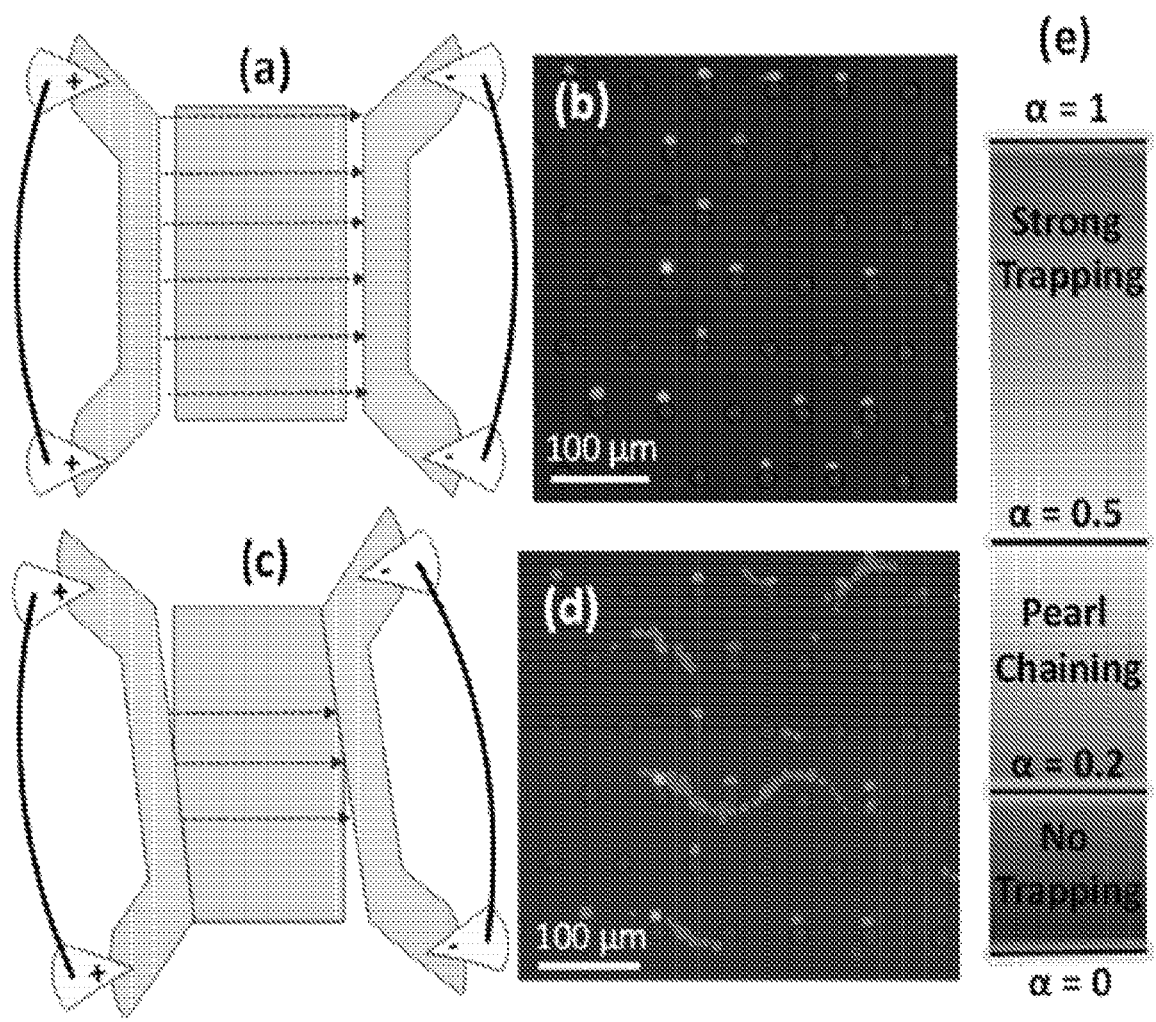
FIG. 20 comprising sub-panes (a)-(e), hereinafter referenced to as FIGS. 20A, 20B, 20C, 20D, and 20E, shows diagrams illustrating correlation of parasitic voltage drop characteristics to DEP trapping in accordance with an illustrative embodiment.

Specifically, FIG. 20 comprising sub-panes (a)-(e), now referenced herein as FIGS. 20A, 20B, 20C, 20D, and 20E, shows diagrams illustrating correlation of parasitic voltage drop characteristics to DEP Trapping in accordance with an illustrative embodiment. FIG. 20A shows a properly fabricated device (i.e., well-aligned). FIG. 20B shows the same device design that is improperly fabricated. FIG. 20C shows an alteration field intensity due to distribution of field lines in the sample channel. Hence, while the higher field intensity at well-aligned sample channels leads to strong DEP trapping, as apparent from the trapping single-cells per insulating post (FIG. 20B), the lower field intensity in devices with small angular mis-alignments leads to "pearl chaining" (FIG. 20D), since field interaction of cells at the posts is unable to overcome cell-cell dipole interactions. The degree of misalignment induced errors and its influence on parasitic voltages can be discerned based on impedance responses, since the barrier capacitance on one side is altered versus the other side due to misalignment. Since capacitances added in series are dominated by the lower capacitance, the net capacitance of this device is lowered versus the well-aligned device.

Indeed, the misalignment causes $f_0$ to be shifted to higher frequencies so that the low frequency (sub-MHz) region is not available for DEP manipulation. As shown in FIGS. 19A and 19C, the impedance response of the mis-aligned device filled with low salt media in the sample channel resembles characteristics of a well-aligned devices filled with a high salt media. The impedance response further highlight the inability of an improperly microfabricated device that has misalignment defects in providing effective DEP manipulation. Indeed, based on such impedance analysis, the study extracted the relevant circuit parameters to assess the device properties.

As noted above, FIG. 18B shows microfabricated device fabricated with lithography errors. In FIG. 18B, the defect caused the sample channel to be narrowed (e.g. having lower electrical length in field direction), which caused a reduction of $R_{ch}$ (e.g., to be comparable to that of the electrode channel ($R_e$)). To this end, even though FIG. 19B shows the well-aligned device layers having a barrier capacitance of 3.5 pF that is conducive to DEP manipulation beyond 100 kHz, FIG. 19D further shows that the voltage fraction available for electrokinetic manipulation dropped-off at high frequencies rather than reaching a steady-state level close to unity. Indeed, the characteristics of the impedance responses of FIGS. 19B and 19D resemble somewhat the simulated responses of the circuits shown in line "iii" in FIG. 15B and line "iii" in FIG. 15D. Such similarity provides validation of the use if the circuit model "iii" of FIG. 15A to this particular defective device geometry.

Based on impedance analysis, the study extracted the relevant circuit parameters and are summarized in Table 1.

Table 1 shows a fitted circuit parameters determined from measured impedance responses of properly and improperly fabricated micro-devices, including parameters for a properly device ("Aligned"), the same device design but fabricated with misalignments ("Misaligned"), and the same device design but fabricated with lithographic errors ("Narrow") (e.g. having narrowed sample channel layers).

TABLE 1

| Device Type | Aligned | Misaligned | Narrow |
|---|---|---|---|
| σ (media) | 15 S/m | 0.1 S/m | 0.1 S/m | 0.1 S/m |
| $f_0$ | 600 KHz | 74 KHz | No dispersion | 160 KHz |

TABLE 1-continued

| Device Type | Aligned | | Misaligned | Narrow |
|---|---|---|---|---|
| $f_1$ | 8.3 MHz | 0.95 MHz | No dispersion | 0.4 MHz |
| $f_2$ | No dispersion | | No dispersion | 7.7 MHz |
| $C_b$ | 4.7 pF | 5 pF | 0.35 pF | 3.5 pF |
| $R_{ch}$ | 63 KΩ | 470 KΩ | 450 KΩ | 250 KΩ |
| $C_p$ | 0.3 pF | 0.35 pF | 0.5 pF | 1.6 pF |
| $R_e$ | ~1 KΩ | 30 KΩ | 30 KΩ | 33 KΩ |
| $C_e$ | 0.2 pF | 0.2 pF | 0.25 pF | 0.6 pF |
| Max α | 90% | 90% | ~63% | ~20% |

Using Table 1, defective microstructure responsible for a given error can be identified to provide a quantitative assessment of a given microfluidic device as well to quantify the influence of such defects to a given microstructure. For instance, misalignment of the sample channel to electrode channels can be observed to significantly decrease the barrier capacitance ($C_b$) from 5 pF to 0.35 pF, which can be used to estimate the degree of misalignment. And, lithography-related channel width alterations that narrow the sample channel can be observed to cause a reduction in sample channel resistance from 470 kΩ to 250 kΩ. This observation can further be used to estimate a larger fold channel width (e.g., 1.88× larger fold width) in the device of FIG. 18A as compared to the device of FIG. 18B.

Figure 21A:
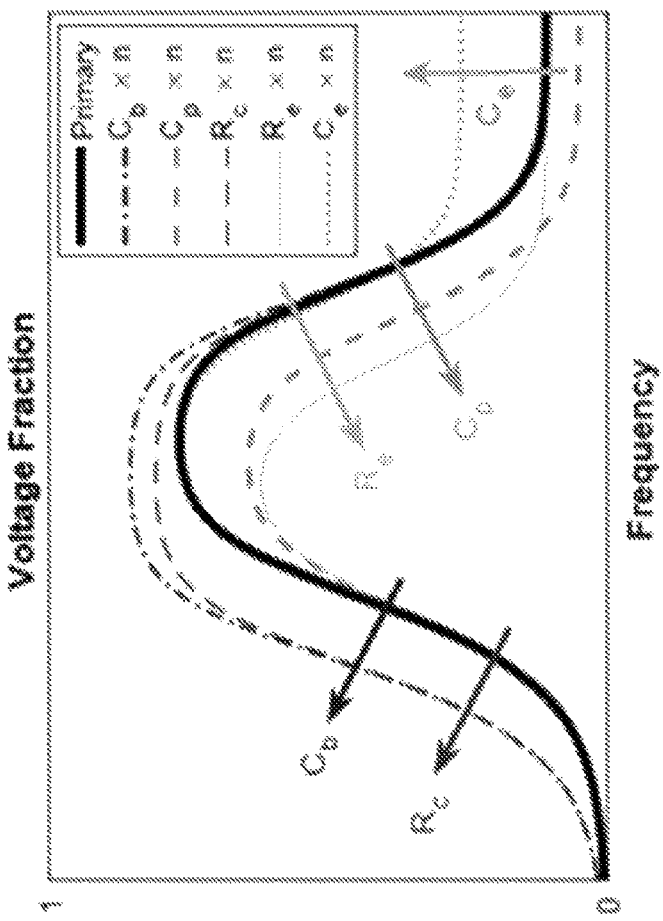
FIGS. 21A and 21B show experimental results to optimize voltage fraction characteristics of a DEP microfluidic device in accordance with an illustrative embodiment.
Figure 21B:
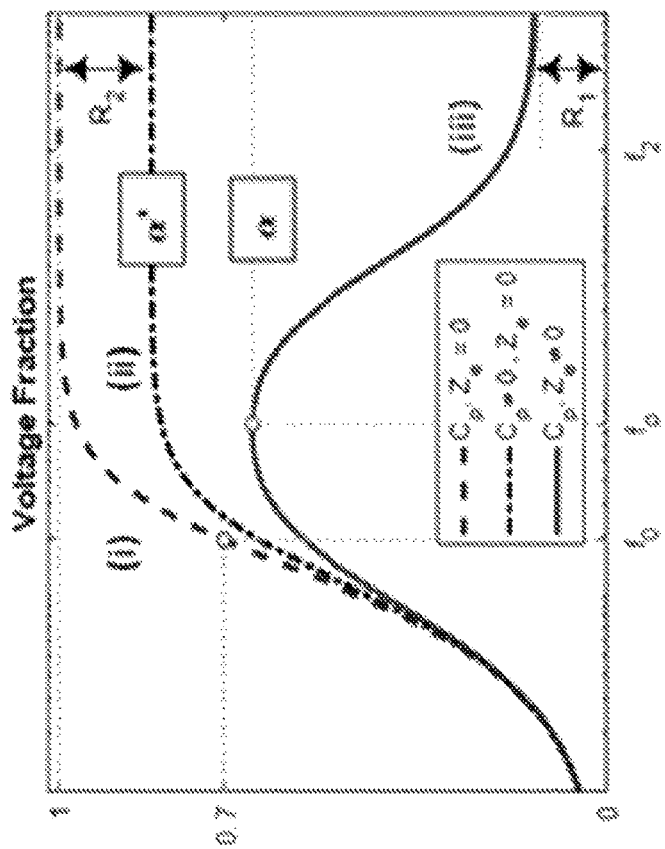

Optimizing Architecture to Maximize Voltage Fraction for DEP:

FIGS. 21A and 21B show experimental results to optimize voltage fraction characteristics of a DEP microfluidic device in accordance with an illustrative embodiment. FIG. 21A shows the influence of various device parameters, and FIG. 21B shows their effect on maximizing voltage fraction for electrokinetic manipulation over a wide frequency range.

As shown in FIGS. 21A and 21B, several criterion may be modulated to optimize device architecture to maximize the voltage fraction available for contactless dielectrophoretic (cDEP) manipulation over a wide frequency range. FIGS. 21A and 21B show design consideration for a device having a voltage fraction that reaches a value as close to unity as possible over a large frequency bandwidth. In FIG. 21A, a baseline device is shown as "Primary". To create a wide frequency window for effective cDEP manipulation, devices with geometries that enable higher $C_b$ and $R_{ch}$ are desired as well as geometries that lower $C_p$, $R_e$, and $C_e$, are preferred.

Per FIG. 21A, the optimization of the device can be achieved by, for example: (1) enhancing the overlap area between the electrode and sample channels, as well as reducing width of the insulating barrier to increase $C_b$; (2) lengthening the sample channel in direction of the electric field (or widening it based on top view) to increase $R_{ch}$; and (3) widening the electrode channels and reducing their length to reduce $R_e$, especially in comparison to $R_{ch}$. FIG. 21B shows the effect of these device parameters on the voltage fraction available for cDEP manipulation per the circuit models ("i"-"iii") of FIG. 15A. For the simplest model ("i") where parasitic capacitances in the sample channel ($C_p$) and impedances in the electrode channel ($Z_e$) are zero, the voltage fraction reached a 70% value at the first cut-off frequency ($f_0$). In the model ("iii") where $C_p$ and $Z_e$ are significant, the voltage fraction plot exhibited a local maximum of at the frequency ($f_p$) that can be computed by Equations 1 and 2.

$$f_p = \frac{1}{2\pi}\sqrt{\frac{1}{R_e R_{ch} C_b C_p}} \quad \text{(Equation 1)}$$

$$\alpha = \frac{1}{\left(1 + \frac{C_p}{C_b} + \frac{R_e}{R_{ch}}\right)} \quad \text{(Equation 2)}$$

At frequencies beyond $f_p$, the "Voltage Fraction" plot declined to a finite non-zero value ($R_1$) that only depended on capacitive components of the model. The value of $R_1$ can be calculated using Equation 3.

$$R1 = \frac{1}{1 + \frac{C_p}{C_b} + \frac{C_p}{C_e}} \quad \text{(Equation 3)}$$

While the maximum voltage fraction reached 100% for the simplest model ("i") of FIG. 15A, Equation 3 shows a reduction of $R_2 = C_p/(C_b + C_p)$ for the case of model ("ii"), to yield a maximum voltage fraction of $\alpha = C_b/(C_b + C_p)$ at higher frequencies. For the circuit models ("ii") and ("iii") of FIG. 15A that include parasitic capacitances and impedances, the corresponding voltage fraction showed drops that are solely determined by the parameter.

Indeed, the study provides a circuit methodology for measuring the net impedance of a microfluidic device, at the voltage and frequency conditions used in contactless dielectrophoresis, so that device architecture can be optimized to maximize electrokinetic manipulation. To enable sensitive impedance measurement, the circuit included a high-gain amplifier with 0.1 dB gain flatness up to 100 MHz, so that a fast comparator can be used to detect amplitude of the measured signal based on charging level of the storage capacitor and phase can be detected by converting signals to digital streams. The study further showed that the impedance response can be used to characterize the fidelity of each relevant microfabricated device geometry and to optimize its architecture for ensuring that a maximum fraction of the applied voltage is available for electrokinetic manipulation. Using the example of a standard contactless dielectrophoresis device, an optimized structure can be designed by: (1) having the insulating barrier between the electrode and sample channels of low width (10-15 μm) and high depth (≥100 μm), which can be assessed based on a high enough barrier capacitance (3-5 pF) for enabling high field penetration onwards from low cut-off frequencies (~50 kHz); (2) improving the fraction of applied voltage that is available for electrokinetic manipulation that reducing effects of parasitic capacitance ($C_p$) in the sample channel and parasitic resistance in the electrode channel ($R_e$), which can be lowered by increasing electrical length along sample channel (to reduce $C_p$ and increase $R_{ch}$) and widening the electrode channel (to reduce $R_e$); (3) assessing for microfabrication errors, such as interlayer channel width variations or mis-alignment, e.g., by fitting the measured impedance responses to determine circuit parameters that can be used to identify and quantify the particular feature of the device geometry that was altered.

Indeed, while the study was focused on impedance-based assessment of microfluidic devices designed for contactless dielectrophoresis, the principles and methodologies disclosed herein can be applied towards other microfluidic structures that are designed for other forms of electrokinetic manipulation, as well as for manipulation under acoustic or inertial force fields, e.g., where there is a need to assess microstructure fidelity.

Discussion

As discussed above, electrical fields, e.g., as generated by electric-field-generating structure (e.g., 108), are widely used within microfluidic devices to selectively polarize[1] and manipulate[2] micro- and nanoscale objects[3] using dielectrophoresis (DEP), such as biomolecules[4], viruses [5], bacteria[6], mammalian cells[7], multi-cell aggregates [8] and aqueous droplet suspensions in oil[9],[10]. Because electrical fields are facile to integrate within microfluidic channels to locally cause particle deflection from flow streamlines and can enable frequency selective polarization of the micro- or nanoscale objects in a label-free manner based on the conductivity and permittivity of their contents, microfluidic devices configured with electric-field-generating structures (e.g., 108) are preferably in used in many applications. The electric-field-generating structures (e.g., 108) in many embodiments includes both an electrode (e.g., 110) and an insulating barrier (e.g., 112). The insulating barriers (e.g., 112) are used to place the electrodes outside the sample channel region, e.g., to prevent electric field-induced damage to the biological object that is being manipulated, e.g., due to electrolysis, electrode fouling, and pH gradient effects. Indeed, the electric field generated from a given electrode (e.g., 110) located in a microfluidic channel is often applied through the insulating barrier (e.g., 112) that isolates the electrode region from the sample manipulation region (e.g., 106). Example of such configurations may be found in microfluidic chips configured for contactless dielectrophoresis (cDEP), e.g., as described in [14]; bipolar electrode DEP, e.g., as described in [15]; passivated electrode DEP, e.g., as described in [16]; electrowetting on dielectric, e.g., as described in [17]; and droplet manipulation systems, e.g., as described in [18],[19].

Electric-field-generating structures (e.g., 108) have, in some embodiments, optimal field penetration that occurs above a cut-off frequency where the capacitor representing the insulating barrier allows for field passage, while resistance and capacitance in the sample and electrode channels can become important at higher frequencies. These parasitic voltage drops may limit fraction of the applied voltage available for electrokinetic particle manipulation[18]. That is, parasitic voltage drops can limit the net fraction of applied voltage available for particle manipulation[20]. The exemplary system (e.g., 100) provides an impedance-based method (e.g., an on-chip impedance-based method) to quantify these voltage drops, e.g., during DEP, for monitoring the microfluidic chip and rapidly informing decisions on particle manipulation.

The level of field penetration and its frequency response through the insulating barrier, as well as fraction of the applied voltage that is available for electrokinetic manipulation, depend strongly on fidelity of the microfabricated structures, such as barrier thickness, surface area and surface charge[21], and architecture of the electrode and sample chambers. However, these factors that ultimately determine impedance of the microfluidic device are often not well-controlled during device fabrication, assembly and application. For instance, barrier thickness, which is determined by the rotational rate used for spin coating of the polymer layers, and barrier surface area, which is determined by the alignment overlap during lithography for the respective polymer layers, can exhibit significant variations (±15%), especially for PDMS layers[22],[23]. Furthermore, control of the surface charge level and its distribution at the neighboring interfaces of the electrode and sample channels is often restricted to merely ensuring that the respective interfaces are hydrophilic, which is insufficient since materials, such as PDMS exhibit time-dependent hydrophobic recovery[24]. Current methods to quantify the efficacy and frequency response of field penetration through the insulating barrier are based on trapping assessments in the sample chamber using model particles.

However, such techniques are unable to quantify parasitic voltage drops, and the frequency region with model particles is different from that of target cells, such as tumor [24], immune [25] or stem cells [26]. There has been some prior work on impedance measurements to monitor electrophoretic mobility [27] and gauge electrical stimulation of tumor cells [28]. However, the measurements were carried out at low frequencies (~kHz range) and using bulky impedance analyzers, rather than by on-chip monitoring. This limits the feedback ability to inform on-chip manipulation decisions. Because dielectrophoresis can enable selective deflection of cells over a wide frequency range (e.g., 0.1-10 MHz), on-chip impedance measurement, in some embodiments, for monitoring and controlling microfluidic manipulation are configured to operate over such range.

Since micro- and nanoscale objects are often valuable samples of rare biological cells (tumor[25], immune[26] or stem cells[27]), standard dielectric particles are often applied to reduce sample wastage, but they can only assess the field-induced manipulation performance within a limited range of fields and frequencies that are determined by size and dielectric dispersion of the model particles. At field levels below the critical level needed for particle manipulation and below the cut-off frequency of the insulating barrier, it is not possible to assess the level and frequency response of field penetration, which can vary significantly for each device based on material and fabrication conditions.

While the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the disclosure (and claims), including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive.

For example, the exemplary method and system using impedance phase and/or amplitude contrast may be used in conjunction with other contrast quantification available in the art, including image analysis-based quantification. Similarly, the exemplary method and system may be used with label-free as well as labeled samples in labeled separation and cytometry (e.g., verification, etc.). Similarly, the exemplary method and system may be used with low-throughput systems.

Indeed, the exemplary method and system may be used in combination with, and not limited to, system and method described in International Patent Application Serial No. PCT/US2017/5 028607, entitled "SYSTEMS FOR ISOLATING AND TRANSPLANTING PANCREATIC ISLETS", filed Apr. 20, 2017; Publication No. WO 2017/184854, Oct. 26, 2017; U.S. Utility patent application Ser. No. 15/515,528, entitled "IDENTIFICATION AND MONITORING OF CELLS BY DIELECTROPHORETIC TRACKING OF ELECTROPHYSIOLOGY AND PHENOTYPE", filed Mar. 29, 2017; Publication No. US-2017-0218424-A1, Aug. 3, 2017; International Patent Application Serial No. PCT/US2015/055021, entitled "IDENTIFICATION AND MONITORING OF CELLS BY DIELECTROPHORETIC TRACKING OF ELECTROPHYSIOLOGY AND PHENOTYPE", filed Oct. 9, 15 2015; Publication No. WO2016057974, Apr. 14, 2016; J. A. Kashatus, et al., "Erk2 Phosphorylation of Drp1 Promotes Mitochondrial Fission and MAPK-Driven Tumor Growth", Molecular Cell 2015, 57 (3), 537-551; A. Rohani, et al., "Label-free quantification of alterations in intracellular mitochondrial dynamics using dielectrophoresis", Analytical Chemistry 2017, 89 (11), 20 5757-5764; U.S. Patent Application Publication No. US 2012/0142032 A1, Morgan, et al., "Multi-frequency impedance method and apparatus for discriminating and counting particles expressing a specific marker", Jun. 7, 2012; Tao Sun, et al., "Single-cell microfluidic impedance cytometry: a review", 25 Microfluidics and Nanofluidics, April 2010, Vol. 8, Issue 4, pp 423-443; European Patent Application Publication No. EP 2259044 A1, Koninklijke Phillips, NV, "Multi-frequency impedance method and apparatus for discriminating and counting particles expressing a specific marker", Dec. 8, 2010; U.S. Pat. No. 10,024,780 B2, Shah, et al., "Methods for Detecting Events in a Flow Cytometer", Jul. 17, 2018; and U.S. Pat. No. 5,631,165, Chupp, et al., "Method for Performing Automated Hematology and Cytometry Analysis", May 20, 1997; U.S. Utility patent application Ser. No. 16/095,097, entitled "SYSTEMS FOR ISOLATING AND TRANSPLANTING PANCREATIC ISLETS", filed Oct. 19, 2018; International Patent Application Serial No. PCT/US2017/028607, entitled "SYSTEMS FOR ISOLATING AND TRANSPLANTING PANCREATIC ISLETS", filed Apr. 20, 2017; Publication No. WO 2017/184854, Oct. 26, 2017; U.S. Utility patent application Ser. No. 15/515,528, entitled "IDENTIFICATION AND MONITORING OF CELLS BY DIELECTROPHORETIC TRACKING OF ELECTROPHYSIOLOGY AND PHENOTYPE", filed Mar. 29, 2017; Publication No. US-2017-0218424-A1, Aug. 3, 2017; International Patent Application Serial No. PCT/US2015/055021, entitled "IDENTIFICATION AND MONITORING OF CELLS BY DIELECTROPHORETIC TRACKING OF ELECTROPHYSIOLOGY AND PHENOTYPE", filed Oct. 9, 2015; Publication No. WO2016057974, Apr. 14, 2016; U.S. Utility patent application Ser. No. 13/564,102, entitled "Method of Local Electro-Magnetic Field Enhancement of Terahertz (THz) Radiation in Sub-Wavelength Regions and Improved Coupling of Radiation to Materials through the Use of the Discontinuity Edge Effect", filed Aug. 1, 2012; U.S. Pat. No. 8,525,115, issued Sep. 3, 2013; U.S. Utility patent application Ser. No. 12/530,304, entitled "Method of Local Electro-Magnetic Field Enhancement of Terahertz (THz) Radiation in Sub Wavelength Regions and Improved Coupling of Radiation to Materials through the Use of the Discontinuity Edge Effect", filed Sep. 8, 2009; U.S. Pat. No. 8,309,930, issued Nov. 13, 2012; International Patent Application Serial No. PCT/US2008/055962, entitled "Method of Local Electro-Magnetic Field Enhancement of Terahertz (THz) Radiation in Sub Wavelength Regions and Improved Coupling of Radiation to Materials through the Use of the Discontinuity Edge Effect", filed Mar. 5, 2008; Publication No. WO 2008/109706, Sep. 12, 2008; and International Patent Application Serial No. PCT/US2019/53242, entitled "Multiplexed On-Chip Impedance Cytometry System and Method," filed Sep. 26, 2019, each of which is incorporated by reference herein in its entirety.

Unless clearly stated otherwise, when any number or range is described herein, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

In addition, an aspect of an embodiment of the present invention provides, but not limited thereto, a circuit (that may be implemented as a system, method and computer readable medium) for quantifying the level and frequency response of electrical field penetration for optimizing particle manipulation in microfluidic devices.

In addition, an aspect of an embodiment of the present invention provides, but not limited thereto, an impedance-based assessment (implemented by a system, method and computer readable medium) of fidelity of microstructure device geometry for optimizing microfluidic electrokinetic manipulation.

In addition, an aspect of an embodiment of the present invention provides, but not limited thereto, a quality control check (implemented by a system, method and computer readable medium) that confirms the voltage and frequency conditions experienced inside a microfluidic device to match those set on the controller.

Moreover, it should be appreciated that any of the components or modules referred to with regards to any of the present invention embodiments discussed herein, may be integrally or separately formed with one another. Further, redundant functions or structures of the components or modules may be implemented. Moreover, the various components may be communicated locally and/or remotely with any user or machine/system/computer/processor. Moreover, the various components may be in communication via wireless and/or hardwire or other desirable and available communication means, systems and hardware. Moreover, various components and modules may be substituted with other modules or components that provide similar functions.

It should be appreciated that the device and related components discussed herein may take on all shapes along the entire continual geometric spectrum of manipulation of x, y and z planes to provide and meet the environmental, anatomical, and structural demands and operational requirements. Moreover, locations and alignments of the various components may vary as desired or required.

It should be appreciated that various sizes, dimensions, contours, rigidity, shapes, flexibility and materials of any of the components or portions of components in the various embodiments discussed throughout may be varied and utilized as desired or required.

It should be appreciated that while some dimensions are provided on the aforementioned figures, the device may constitute various sizes, dimensions, contours, rigidity, shapes, flexibility and materials as it pertains to the components or portions of components of the device, and therefore may be varied and utilized as desired or required.

Although example embodiments of the present disclosure are explained in detail herein, it is to be understood that other embodiments are contemplated. Accordingly, it is not intended that the present disclosure be limited in its scope to the details of construction and arrangement of components set forth in the following description or illustrated in the drawings. The present disclosure is capable of other embodiments and of being practiced or carried out in various ways.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the disclosure, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

The following patents, applications and publications as listed below and throughout this document are hereby incorporated by reference in their entirety herein.

LIST OF REFERENCES

[1] Jones, T. B., Electromechanics of particles. Cambridge University Press (2005).
[2] Morgan, H.; Green, N. G., AC electrokinetics. Research Studies Press (2003).
[3] Green, N. G.; Ramos, A.; Morgan, H., "Ac electrokinetics: a survey of sub-micrometre particle dynamics," Journal of Physics D: Applied Physics, 33 (6), 632 (2000).
[4] Rohani, A.; Sanghavi, B. J.; Salahi, A.; Liao, K.-T.; Chou, C.-F.; Swami, N. S., "Frequency-selective electrokinetic enrichment of biomolecules in physiological media based on electrical double-layer polarization," Nanoscale, 9 (33), 12124-12131 (2017)
[5] Madiyar, F. R.; Bhana, S.; Swisher, L. Z.; Culbertson, C. T.; Huang, X.; Li, J., "Integration of a nanostructured dielectrophoretic device and a surface-enhanced Raman probe for highly sensitive rapid bacteria detection," Nanoscale, 7 (8), 3726-3736 (2015).
[6] Fernandez, R. E.; Rohani, A.; Farmehini, V.; Swami, N. S., "Microbial analysis in dielectrophoretic microfluidic systems," Analytica chimica acta, 966, 11-33 (2017).
[7] Rohani, A.; Moore, J. H.; Kashatus, J. A.; Sesaki, H.; Kashatus, D. F.; Swami, N. S., "Label-free quantification of intracellular mitochondrial dynamics using dielectrophoresis," Analytical chemistry 89 (11), 5757-5764 (2017).
[8] Burgarella, S.; Merlo, S.; Figliuzzi, M.; Remuzzi, A., "Isolation of L angerhans islets by dielectrophoresis," Electrophoresis, 34 (7), 1068-1075 (2013).
[9] Hunt, T. P.; Issadore, D.; Westervelt, R. M., "Integrated circuit/microfluidic chip to programmably trap and move cells and droplets with dielectrophoresis," Lab on a Chip, 8 (1), 81-87 (2008).
[10] Barbulovic-Nad, I.; Xuan, X.; Lee, J. S.; Li, D., "DC dielectrophoretic separation of microparticles using an oil droplet obstacle," Lab on a Chip, 6 (2), 274-279 (2006).
[11] Walling, M. A.; Shepard, J. R., "Cellular heterogeneity and live cell arrays," Chemical Society Reviews, 40 (7), 4049-4076 (2011).
[12] Bruus, H.; Dual, J.; Hawkes, J.; Hill, M.; Laurell, T.; Nilsson, J.; Radel, S.; Sadhal, S.; Wiklund, M., "Forthcoming Lab on a Chip tutorial series on acoustofluidics: Acoustofluidics—exploiting ultrasonic standing wave forces and acoustic streaming in microfluidic systems for cell and particle manipulation," Lab on a Chip, 11 (21), 3579-3580 (2011).
[13] Varhue, W. B.; Langman, L.; Kelly-Goss, M.; Lataillade, M.; Brayman, K. L.; Peirce-Cottler, S.; Swami, N. S., "Deformability-based microfluidic separation of pancreatic islets from exocrine acinar tissue for transplant applications," Lab on a Chip, 17 (21), 3682-3691 (2017).
[14] Shafiee, H.; Caldwell, J. L.; Sano, M. B.; Davalos, R. V., "Contactless dielectrophoresis: a new technique for cell manipulation," Biomedical microdevices, 11 (5), 997 (2009).
[15] Li, M.; Anand, R. K., "High-throughput selective capture of single circulating tumor cells by dielectrophoresis at a wireless electrode array," Journal of the American Chemical Society, 139 (26), 8950-8959 (2017).
[16] Zellner, P.; Shake, T.; Sahari, A.; Behkam, B.; Agah, M., "Offchip passivated-electrode, insulator-based dielectrophoresis (OiDEP)," Analytical and bioanalytical chemistry, 405 (21), 6657-6666 (2013).
[17] Choi, K.; Ng, A. H.; Fobel, R.; Wheeler, A. R., "Digital microfluidics," Annual review of analytical chemistry, 5, 413-440 (2012).
[18] Link, D. R.; Grasland-Mongrain, E.; Duri, A.; Sarrazin, F.; Cheng, Z.; Cristobal, G.; Marquez, M.; Weitz, D. A., "Electric control of droplets in microfluidic devices,". Angewandte Chemie International Edition, 45 (16), 2556-2560 (2006).
[19] Baret, J.-C.; Miller, O. J.; Taly, V.; Ryckelynck, M.; El-Harrak, A.; Frenz, L.; Rick, C.; Samuels, M. L.; Hutchison, J. B.; Agresti, J. J., "Fluorescence-activated droplet sorting (FADS): efficient microfluidic cell sorting based on enzymatic activity," Lab on a Chip, 9 (13), 1850-1858 (2009).
[20] Zhu, X.; Tung, K.-W.; Chiou, P.-Y., "Heavily doped silicon electrode for dielectrophoresis in high conductivity media," Applied Physics Letters, 111 (14), 143506 (2017).
[21] Sano, M. B.; Salmanzadeh, A.; Davalos, R. V., "Multilayer contactless dielectrophoresis: Theoretical considerations," Electrophoresis, 33 (13), 1938-1946 (2012).
[22] Moraes, C.; Sun, Y.; Simmons, C. A., "Solving the shrinkage-induced PDMS alignment registration issue in multilayer soft lithography," Journal of micromechanics and microengineering, 19 (6), 065015 (2009).
[23] Hanson, C.; Vargis, E., "Alternative cdep design to facilitate cell isolation for identification by Raman spectroscopy," Sensors, 17 (2), 327 (2017).
[24] Bodas, D.; Khan-Malek, C., "Hydrophilization and hydrophobic recovery of PDMS by oxygen plasma and chemical treatment—An SEM investigation," Sensors and Actuators B: Chemical, 123 (1), 368-373 (2007).
[25] Salmanzadeh, A.; Romero, L.; Shafiee, H.; Gallo-Villanueva, R. C.; Stremler, M. A.; Cramer, S. D.; Davalos, R. V., "Isolation of prostate tumor initiating cells (TICs) through their dielectrophoretic signature," Lab on a Chip, 12 (1), 182-189 (2012).
[26] Huang, Y.; Wang, X.-B.; Gascoyne, P. R.; Becker, F. F., "Membrane dielectric responses of human T-lymphocytes following mitogenic stimulation," Biochimica et Biophysica Acta (BBA)-Biomembranes, 1417 (1), 51-62 (1999).
[27] Adams, T. N.; Jiang, A. Y.; Vyas, P. D.; Flanagan, L. A., "Separation of neural stem cells by whole cell membrane capacitance using dielectrophoresis," Methods, 133, 91-103 (2018).
[28] Dual, J.; Hahn, P.; Leibacher, I.; Möller, D.; Schwarz, T., "Acoustofluidics 6: Experimental characterization of ultrasonic particle manipulation devices," Lab on a Chip, 12 (5), 852-862 (2012).

[29] Hammarström, B.; Evander, M.; Wahlstrom, J.; Nilsson, J., "Frequency tracking in acoustic trapping for improved performance stability and system surveillance," Lab on a Chip, 14 (5), 1005-1013 (2014).
[30] Farmehini, V.; Rohani, A.; Su, Y.-H.; Swami, N. S., "A wide-bandwidth power amplifier for frequency-selective insulator-based dielectrophoresis," Lab on a Chip, 14 (21), 4183-4187 (2014).
[31] Horowitz, P.; Hill, W.; Robinson, I., The art of electronics. Cambridge university press Cambridge Vol. 2 (1980). [32] McLucas, J., "Precision peak detector uses no precision components," CAHNERS-DENVER PUBLISHING CO (2004).
[33] Gardner, F. M., Phaselock techniques. John Wiley & Sons (2005).
[34] Ott, H. W., Electromagnetic compatibility engineering. John Wiley & Sons (2011).

What is claimed is:

1. A method comprising:
    providing a microfluidic chip, the microfluidic chip comprising a microfluidic channel with one or more electric-field-generating structures located therein, including a first electric-field-generating structure, wherein the one or more electric-field-generating structures is configured to selectively polarize or manipulate biologic or particle components flowing within the microfluidic channel; and
    measuring, via an on-chip impedance sensing element, impedance spectra associated with at least one internal capacitive structure of the first electric-field-generating structure or characteristic of the biologic or particle components, and determining, via a processor or logic circuit, one or more parameters associated with the at least one internal capacitive structure, wherein the one or more parameters is selected from the group consisting of:
        an associated thickness of the at least one capacitive structure;
        a surface area size of the at least one internal capacitive structure;
        a surface charge property of the at least one internal capacitive structure;
        an architecture feature of the at least one internal capacitive structure; and
        a size of a portion of microfluidic channel to which the first electric-field-generating structure is located;
    wherein the measured impedance spectra is used at least for one of i) control of the polarization or manipulation of the biologic or particle components when flowing through the microfluidic channel and ii) geometric or functional quantification of the at least one internal capacitive structure or of the microfluidic chip.

2. The method of claim 1, further comprising:
    triggering, by a processor or control circuit, controls of media conditions, polarization, or manipulation of the biologic or particle components when flowing through the microfluidic channel based on the measured impedance spectra.

3. The method of claim 2, further comprising:
    determining, via a processor or logic circuit, one or more parameters associated with the at least one internal capacitive structure or the characteristic of the biologic or particle components, wherein the determination is performed by a fitting operation, performed via the processor or logic circuit, of the measured impedance spectra to an equivalent circuit model that at least include the first electric-field-generating structure or a portion thereof.

4. The method of claim 1, wherein the impedance spectra is measured by:
    applying an impedance interrogating signal having a power level and a frequency range corresponding to those associated with the control of the media condition, polarization, or manipulation of the biologic or particle components; and
    measuring a resulting voltage resulting from the applied impedance interrogating signal, wherein the measured resulting voltage has an amplitude and phase properties that defines the impedance spectra.

5. The method of claim 1, wherein the first electric-field-generating structure comprises an electrode portion and an insulating barrier, wherein the insulating barrier corresponds to the at least one internal capacitive structure.

6. The method of claim 5, wherein the electrode portion is configured as at least one of:
    a contactless dielectrophoresis electrode;
    a bi-polar dielectrophoresis electrode;
    a passivated dielectrophoresis electrode;
    an electrowetting on dielectric electrode; and
    a droplet manipulating system electrode.

7. The method of claim 1, wherein the impedance spectra is measured when the biologic or particle components are flowing within the microfluidic channel.

8. The method of claim 1, wherein the impedance spectra is measured when the microfluidic channel is filled with a test media that does not have present biologic or particle components of interest.

9. The method of claim 1,
    wherein the first electric-field-generating structure is used for electrokinetic trapping, acoustic trapping, or dielectrophoresis operation, and
    wherein the functional quantification of at least one internal capacitive structure or the characteristic of the biologic or particle component comprises at least one of:
        a quantification associated with efficacy of the electrokinetic trapping, acoustic trapping, or dielectrophoresis operation;
        a quantification associated with a frequency response of the electrokinetic trapping, acoustic trapping, or dielectrophoresis operation;
        a quantification of parasitic voltage drops of the first electric-field-generating structure;
        a quantification associated with identifying a particle type and its position in the microfluidic channel; and
        a quantification associated with sample transport post-trapping operation.

10. The method of claim 1, wherein the first electric-field-generating structure and corresponding controls are configured for a target cell type selected from the group consisting of tumor cells, immune cells, and stem cells.

11. The method of claim 1, wherein the first electric-field-generating structure and corresponding controls are configured for dielectrophoresis operation having a wide frequency range of at least 1 MHz.

12. The method of claim 1, wherein the measured impedance spectra is used for the control of the selective polarization or manipulation of the biologic or particle components when flowing through the microfluidic channel.

13. The method of claim 1, wherein the measured impedance spectra is used for the geometric or functional quantification of at least one internal capacitive structure of the first electric-field-generating structure or of the microfluidic chip.

14. The method of claim 13, wherein the geometric or functional quantification is used to determine an initialized control setting value used in the control of the microfluidic chip.

15. The method of claim 1, wherein the measured impedance spectra is used for the geometric or functional quantification of at least one internal capacitive structure of the first electric-field-generating structure or the microfluidic chip as part of a quality control assessment operation of the microfluidic chip.

16. The method of claim 1, wherein the measured impedance spectra is used for the geometric or functional quantification of at least one internal capacitive structure of the first electric-field-generating structure or the microfluidic chip to determine a geometry or functional feature of the first electric-field-generating structure that is optimized for maximum trapping operation.

17. The method of claim 1, wherein the microfluidic chip comprises a channeled structure made of a material selected from the group consisting of a polymer and a glass.

18. The method of claim 1, wherein the impedance spectra is measured via active electronic components located on an electronic board that is electrically coupled to the on-chip impedance sensing elements.

19. The method of claim 3, wherein the equivalent circuit model includes:
  a first set of one or more impedance-associated parameters of at least one electrode of the first electric-field-generating structure,
  a second set of one or more impedance-associated parameters of the microfluidic channel, and
  a third set of one or more impedance-associated parameters of a capacitive structure that, at least, includes the at least one internal capacitive structure of the first electric-field-generating structure.

20. A method comprising:
  providing a microfluidic chip, the microfluidic chip comprising a microfluidic channel with one or more electric-field-generating structures located therein, including a first electric-field-generating structure, wherein the one or more electric-field-generating structures is configured to selectively polarize or manipulate biologic or particle components flowing within the microfluidic channel; and
  measuring, via an on-chip impedance sensing element, impedance spectra associated with at least one internal capacitive structure of the first electric-field-generating structure or characteristic of the biologic or particle components, wherein the impedance spectra is measured by:
    applying an impedance interrogating signal having a power level and a frequency range corresponding to those associated with the control of the media condition, polarization, or manipulation of the biologic or particle components; and
    measuring a resulting voltage resulting from the applied impedance interrogating signal, wherein the measured resulting voltage has an amplitude and phase properties that defines the impedance spectra;
  wherein the measured impedance spectra is used at least for one of i) control of the polarization or manipulation of the biologic or particle components when flowing through the microfluidic channel and ii) geometric or functional quantification of the at least one internal capacitive structure or of the microfluidic chip.

21. A method comprising:
  providing a microfluidic chip, the microfluidic chip comprising a microfluidic channel with one or more electric-field-generating structures located therein, including a first electric-field-generating structure, wherein the one or more electric-field-generating structures is configured to selectively polarize or manipulate biologic or particle components flowing within the microfluidic channel; and
  measuring, via an on-chip impedance sensing element, impedance spectra associated with at least one internal capacitive structure of the first electric-field-generating structure or characteristic of the biologic or particle components,
  wherein the measured impedance spectra is used at least for one of i) control of the polarization or manipulation of the biologic or particle components when flowing through the microfluidic channel and ii) geometric or functional quantification of the at least one internal capacitive structure or of the microfluidic chip,
  wherein the first electric-field-generating structure is used for electrokinetic trapping, acoustic trapping, or dielectrophoresis operation, and
  wherein the functional quantification of at least one internal capacitive structure or the characteristic of the biologic or particle component comprises at least one of:
    a quantification associated with efficacy of the electrokinetic trapping, acoustic trapping, or dielectrophoresis operation;
    a quantification associated with a frequency response of the electrokinetic trapping, acoustic trapping, or dielectrophoresis operation;
    a quantification of parasitic voltage drops of the first electric-field-generating structure;
    a quantification associated with identifying a particle type and its position in the microfluidic channel; and
    a quantification associated with sample transport post-trapping operation.

\* \* \* \* \*